(12) United States Patent
Komatsu et al.

(10) Patent No.: US 12,012,432 B2
(45) Date of Patent: Jun. 18, 2024

(54) NUCLEIC ACID COMPLEX, METHOD FOR FORMING NUCLEIC ACID HYBRIDIZATION, PHARMACEUTICAL COMPOSITION, NUCLEIC ACID PROBE, AND COMPLEMENTARY-STRAND NUCLEIC ACID COMPLEX

(71) Applicant: National Institute of Advanced Industrial Science and Technology, Tokyo (JP)

(72) Inventors: Yasuo Komatsu, Sapporo (JP); Yu Hirano, Sapporo (JP); Yasuhiro Mie, Sapporo (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 896 days.

(21) Appl. No.: 16/995,477

(22) Filed: Aug. 17, 2020

(65) Prior Publication Data
US 2021/0032282 A1    Feb. 4, 2021

Related U.S. Application Data

(63) Continuation of application No. 15/532,916, filed as application No. PCT/JP2015/084402 on Dec. 8, 2015, now abandoned.

(30) Foreign Application Priority Data

Dec. 12, 2014  (JP) .................. 2014-251847

(51) Int. Cl.
| | | |
|---|---|---|
| C07H 21/04 | (2006.01) | |
| A61K 31/7088 | (2006.01) | |
| A61K 31/713 | (2006.01) | |
| A61K 48/00 | (2006.01) | |
| C07H 21/02 | (2006.01) | |
| C12N 15/00 | (2006.01) | |
| C12N 15/09 | (2006.01) | |
| C12N 15/113 | (2010.01) | |
| C12Q 1/68 | (2018.01) | |
| C12Q 1/6832 | (2018.01) | |

(52) U.S. Cl.
CPC ......... *C07H 21/04* (2013.01); *A61K 31/7088* (2013.01); *A61K 31/713* (2013.01); *A61K 48/00* (2013.01); *C07H 21/02* (2013.01); *C12N 15/00* (2013.01); *C12N 15/09* (2013.01); *C12N 15/113* (2013.01); *C12Q 1/68* (2013.01); *C12Q 1/6832* (2013.01); *C12N 2310/141* (2013.01); *C12N 2310/321* (2013.01)

(58) Field of Classification Search
CPC ...... C07H 21/04; C07H 21/02; A61K 31/713; A61K 48/00; C12N 15/00; C12N 15/09; C12N 15/113; C12Q 1/68; C12Q 1/6832

USPC .... 435/6.1, 91.1, 91.31, 455, 458; 536/23.1, 536/24.5; 424/9.1

See application file for complete search history.

(56) References Cited

U.S. PATENT DOCUMENTS

| | | | |
|---|---|---|---|
| 5,543,507 A | 8/1996 | Cook | |
| 6,232,463 B1 * | 5/2001 | Cook | ............... C07H 19/16 |
| | | | 536/25.31 |
| 2002/0012913 A1 | 1/2002 | Gunderson | |

FOREIGN PATENT DOCUMENTS

| | | | |
|---|---|---|---|
| JP | 4-506206 | 10/1992 | |
| JP | 7-504438 | 5/1995 | |
| JP | 2000-102384 | 4/2000 | |
| JP | 2002-531105 | 9/2002 | |
| JP | 2014-018143 | 2/2004 | |
| JP | 2006-075082 | 3/2006 | |
| JP | 5196448 B2 * | 5/2013 | ........... C07C 235/16 |
| WO | 90/12020 | 10/1990 | |
| WO | 00/32823 | 6/2000 | |
| WO | 2004/044313 | 5/2004 | |
| WO | 2009/082020 | 7/2009 | |
| WO | WO-2009082020 A1 * | 7/2009 | ........... C07C 235/16 |

OTHER PUBLICATIONS

Ichikawa et al (Chem. Commun., vol. 48, pp. 2143-2145 (2012)) (Year: 2012).*
Koshkin, et al., (1998) "LNA (locked nucleic acids): synthesis of the adenine, cytosine, guanine, 5-methylcytosine, thymine and uracil bicyclonucleoside monomers, oligomerisation, and unprecedented nucleic acid recognition", Tetrahedron 54, 3607-3630.
Obika, et al., (1998) "Stability and structural features of the duplexes containing nucleoside analogues with a fixed-N-type conformation, 2'-O,4'-C-methyleneribonucleosides", Tetrahedron Lett. 39, 5401-5404.
Inoue, et al., (1987) "Synthesis and hybridization studies on two complementary nona (2'O-methyl) ribonucleotides", Nucleic Acids Res., 15, 6131-6148.
Haraguchi, et al., (2009) "Vectors expressing efficient RNA decoys achieve the long-term suppression of specific microRNA activity in mammalian cells", Nucleic Acids Res 37, e43.
Haraguchi, et al., (2012) "A potent 2'-O-methylated RNA-based microRNA inhibitor with unique secondary structures", Nucleic Acids Res 40, e58.
Lennox, et al., (2010) "A direct comparison of anti-microRNA Oligonucleotide Potency", Pharm Res 27 1788-1799.

(Continued)

*Primary Examiner* — Jane J Zara
(74) *Attorney, Agent, or Firm* — HSML P.C.

(57) ABSTRACT

A nucleic acid complex includes a single-stranded nucleic acid and a cross-linked double-stranded nucleic acid including the first nucleic acid strand linked to at least one of the 5' end and the 3' end of the single-stranded nucleic acid and the second nucleic acid strand including a base sequence that is completely or sufficiently complementary to the first nucleic acid strand.

4 Claims, 16 Drawing Sheets
Specification includes a Sequence Listing.

(56) References Cited

OTHER PUBLICATIONS

Vermeulen, et al., (2007) "Double-stranded regions are essential design components of potent inhibitors of RISC function", RNA 13, 732-730.
Ichikawa, et al., "Interstrand cross-link of DNA by covalently linking a pair of abasic sites", Chem. Commun., 2012, vol. 48, pp. 2143-2145.
Mie, et al., "Interstrand cross-links of 2'-O-methyl RNA duplexes and its application to function inhibitors for miRNA", Jul. 15, 2015, 17th RNA meeting in Sapporo, Institute for Genetic Medicine, Hokkaido University, p. 240.
Extended European Search Report issued on Jul. 24, 2018 for related European Patent Application No. 15868164.3.

* cited by examiner

PAGE FOR CHECKING DNA CL PRODUCTS

FIG. 7B

PAGE FOR CHECKING 2'-OME CL PRODUCTS

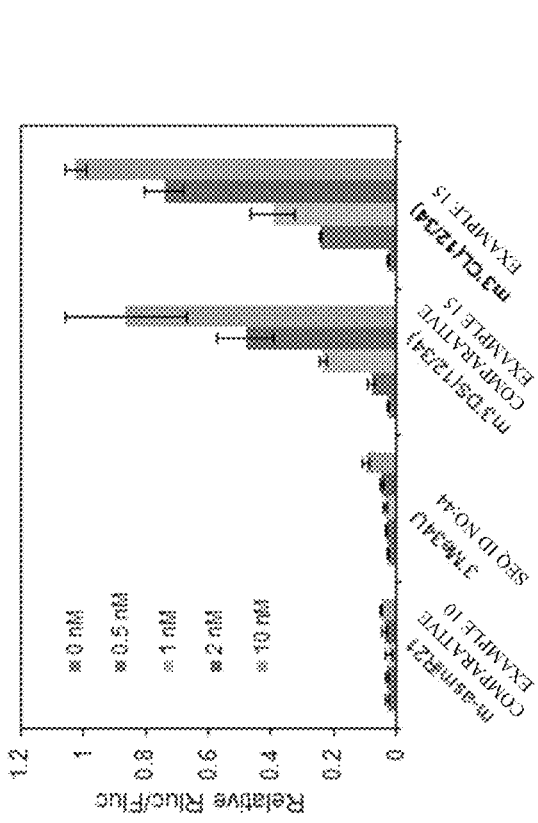
FIG. 11A
FIG. 11B
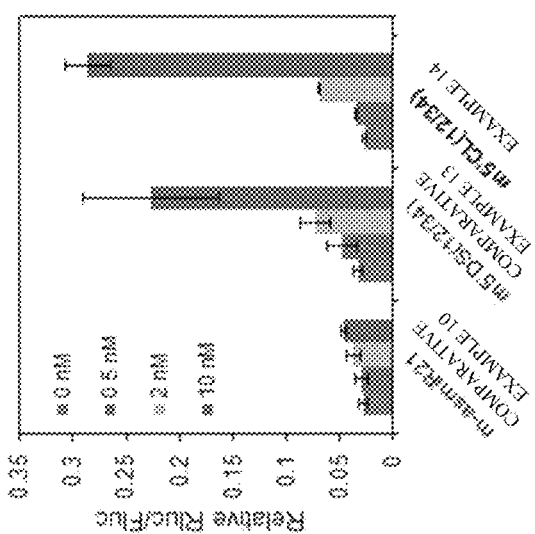
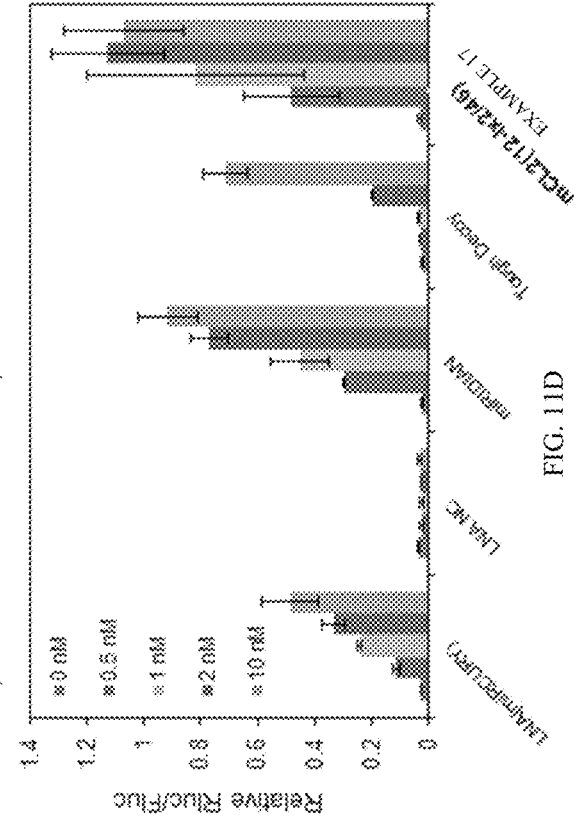
FIG. 11C
FIG. 11D
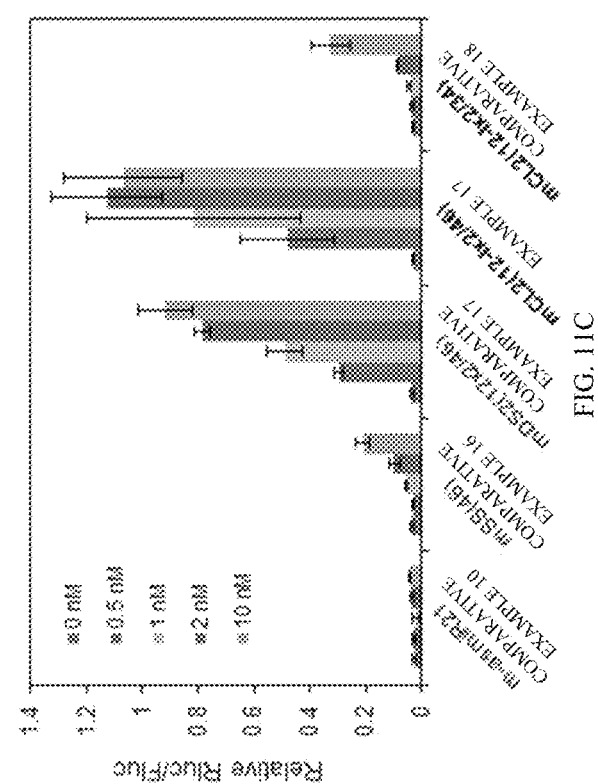

FIG. 12A

COMPARATIVE EXAMPLE 19

```
        5' TAGCTTATCAGACTGATGTTGAGCTTGCxGCTCCG 3'    dC348U
        3' GCCTCGxCGTTCGATCGAATAGTCTGACTACAAGT 5'
```

EXAMPLE 19

```
                                                    d5'CL(12/34)
        5' CGGAGCXGCAGC 3'
        5' TAGCTTATCAGACTGATGTTGAGCTTGCxGCTCCG 3'   dC348U
        3' GCCTCGxCGTCGATCGAATAGTCTGACTACAAGT 5'
                        (X=U)
```

EXAMPLE 20

```
                                                    d5'CL(12/34)
        5' CGGAGCXGCAGC 3'
        5' TAGCTTATCAGACTGATGTTGAGCTTGCxGCTCCG 3'   dcCL(12/34)
        3' CGGAGCXGCAGC 5'
        3' GCCTCGxCGTCGATCGAATAGTCTGACTACAAGT 5'
                        (X=U)
```

FIG. 12B

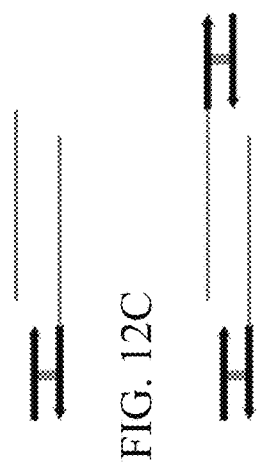

FIG. 12C

FIG. 12D

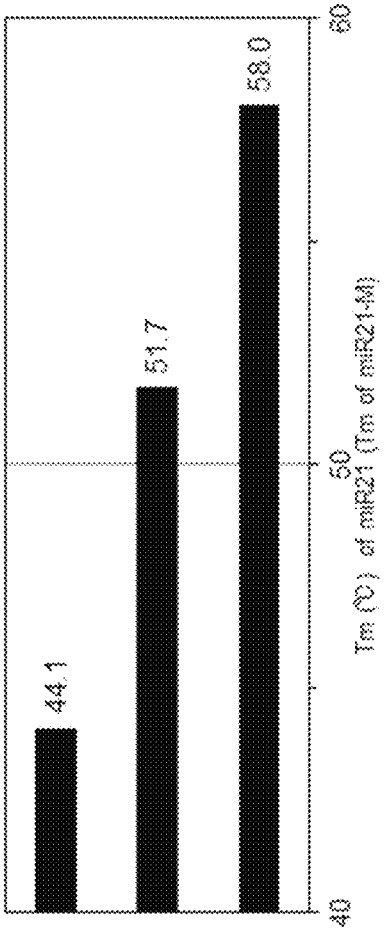

Tm (°C) of miR21 (Tm of miR21-M)

COMPARATIVE EXAMPLE 19: 44.1
EXAMPLE 19: 51.7
EXAMPLE 20: 58.0

NUCLEIC ACID COMPLEX, METHOD FOR FORMING NUCLEIC ACID HYBRIDIZATION, PHARMACEUTICAL COMPOSITION, NUCLEIC ACID PROBE, AND COMPLEMENTARY-STRAND NUCLEIC ACID COMPLEX

TECHNICAL FIELD

The present disclosure relates to nucleic acid complexes, methods of nucleic acid hybridization, pharmaceutical compositions, probes for nucleic acid detection, and complementary strand nucleic acid complexes.

BACKGROUND ART

When nucleic acids are introduced into the body from the outside, the nucleic acid introduced is readily broken down by nucleases present in the blood or body fluids and is therefore unable to stably form hybrids with DNA or RNA that has a target sequence.

In view of this, for the purpose of improving nucleic acid's stability within a living organism, techniques for chemically modifying the nucleic acid have been developed.

Non Patent Literature 1 and 2 have reported that locked nucleic acids (LNAs) developed as modified nucleic acids are highly stabile in hybridization with RNA. In addition, Non Patent Literature 3 has reported chemical modification (2'-O-methyl (2'-OMe) nucleotides) of methylation of the 2' hydroxyl group of the sugar moiety of nucleic acid to be hybridized.

In order to improve the durability of nucleic acids within a living organism, approaches different from the modified nucleic acid have been suggested.

Non Patent Literature 4 and 5 describe that formation of a complementary double stranded nucleic acid structure adjacent to an oligonucleotide sequence that hybridizes with miRNA improves nuclease resistance of the oligonucleotide sequence. In addition, Non Patent Literature 6 and 7 describe that a hairpin loop is designed to form in a complementary double stranded nucleic acid structure formed adjacent to an oligonucleotide sequence that hybridizes with miRNA.

CITATION LIST

Non Patent Literature

Non Patent Literature 1: Koshkin, A., Singh, S., Nielsen, P., Rajwanshi, V., Kumar, R., Meldgaard, M., Olsen, C. E. and Wengel, J. (1998). LNA (locked nucleic acids): synthesis of the adenine, cytosine, guanine, 5-methylcytosine, thymine and uracil bicyclonucleoside monomers, oligomerisation, and unprecedented nucleic acid recognition. Tetrahedron 54, 3607-3630.

Non Patent Literature 2: Obika, S., Nanbu, D., Hari, Y., Andoh, J., Morio, K., Doi, T. and Imanishi, T. (1998). Stability and structural features of the duplexes containing nucleoside analogues with a fixed N-type conformation, 2'-0,4'-C-methyleneribonucleosides. Tetrahedron Lett. 39, 5401-5404.

Non Patent Literature 3: Inoue, H., Hayase, Y., Imura, A., Iwai, S., Miura, K. and Ohtsuka, E. (1987). Synthesis and hybridization studies on two complementary nona(2'-O-methyl)ribonucleotides. Nucleic Acids Res. 15, 6131-6148.

Non Patent Literature 4: Haraguchi, T., Ozaki, Y. & Iba, H. (2009). Vectors expressing efficient RNA decoys achieve the long-term suppression of specific microRNA activity in mammalian cells. Nucleic Acids Res 37, e43.

Non Patent Literature 5: Haraguchi, T., Nakano, H., Tagawa, T., Ohki, T., Ueno, Y., Yoshida, T. & Iba, H. (2012). A potent 2'-O-methylated RNA-based microRNA inhibitor with unique secondary structures. Nucleic Acids Res 40, e58.

Non Patent Literature 6: Lennox, K. A. & Behlke, M. A. (2010). A direct comparison of anti-microRNA oligonucleotide potency. Pharm Res 27, 1788-1799.

Non Patent Literature 7: Vermeulen, A., Robertson, B., Dalby, A. B., Marshall, W. S., Karpilow, J., Leake, D., Khvorova, A. & Baskerville, S. (2007). Double-stranded regions are essential design components of potent inhibitors of RISC function. RNA 13, 723-730.

SUMMARY OF INVENTION

Technical Problem

There have, however, been drawbacks in the methods of Non Patent Literature 1 to 3; and the cost for the synthesis is high in particular when multiple nucleic acids are modified in the oligonucleotide sequence. In addition, the stability of the complementary double stranded nucleic acid structure formed adjacent to the oligonucleotide sequence that hybridizes with miRNA fluctuates according to changes in external factors such as temperature, ionic strength, or pH in the methods of Non Patent Literature 4 to 7; and there have thus been some cases where the complementary double stranded nucleic acid structure dissociates into single strands within a living organism.

The present disclosure was made in light of the above circumstances; and an objective thereof is to provide nucleic acid complexes capable of stably hybridizing with a target nucleic acid, methods of nucleic acid hybridization, pharmaceutical compositions, probes for nucleic acid detection, and complementary strand nucleic acid complexes.

Solution to Problem

In order to achieve the above objective, the nucleic acid complex according to the first aspect of the present disclosure comprises a single-stranded nucleic acid and a cross-linked double-stranded nucleic acid comprising a first nucleic acid strand linked to at least one of the 5' end and the 3' end of the single-stranded nucleic acid and a second nucleic acid strand comprising a base sequence that is completely or sufficiently complementary to the first nucleic acid strand.

The above-mentioned cross-linked double-stranded nucleic acid is, for example, linked to the 5' end of the single-stranded nucleic acid.

The above-mentioned cross-linked double-stranded nucleic acid is, for example, cross-linked by a bond via a sugar of at least one of the first nucleic acid strand and the second nucleic acid strand.

The above-mentioned cross-linked double-stranded nucleic acid is, for example, cross-linked by a bond between sugars of the first nucleic acid strand and the second nucleic acid strand.

The sugars of the first nucleic acid strand and the second nucleic acid strand are, for example, bound by at least one kind of covalent bond selected from the group consisting of an amide bond, an oxime bond, an alkylamide bond, an S—S bond, and a carbon-carbon bond.

The sugars of the first nucleic acid strand and the second nucleic acid strand are, for example, linked by a cross-linking reagent having an aminooxy group or an amino group.

The above-mentioned cross-linking reagent is, for example, a compound represented by general formula 1:

$$R_1\text{—NH—O-}L_1\text{-D-}L_2\text{-A} \quad (1)$$

(wherein
$R_1$ is a protective group of a hydrogen atom, an alkyl group, or an amino group,
D is an aromatic group selected from a substituted or unsubstituted phenylene group, a substituted or unsubstituted anthrylene group, a substituted or unsubstituted naphthylene group, a substituted or unsubstituted phenanthrylene group, a substituted or unsubstituted anthraquinolylene group, and a substituted or unsubstituted acridinylene group, or a $C_{2-10}$ alkyl group,
a substituent of the aromatic group is selected from the group consisting of a halogen atom, a $C_{1-6}$ alkyl group, a nitro group, a cyano group, a $C_{2-6}$ alkenyl group, a $C_{3-10}$ cycloalkyl group, a $C_{1-10}$ alkoxy group, and a $C_{1-10}$ acyl group,
$L_1$ is a direct bond or a divalent group represented by the following general formula 3 or 4:

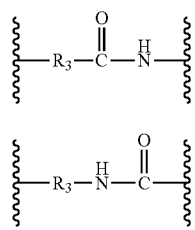

(3)

(4)

(wherein $R_3$ is a $C_{1-9}$ alkylene group or —$(CH_2)_o$—$(OCH_2CH_2)_p$—$(CH_2)_q$—, o to q are each independently an integer of 0 to 15, o+p+q is 1 to 15),
$L_2$ is a direct bond or a divalent group represented by the following general formula 5 or 6:

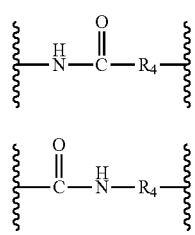

(5)

(6)

(wherein $R_4$ is a $C_{1-9}$ alkylene group or —$(CH_2)_r$—$(OCH_2CH_2)_s$—$(CH_2)_t$—, r to t are each independently an integer of 0 to 15, r+s+t is 1 to 15), and
A is an aminooxy group or a protected aminooxy group)
or a salt thereof.

The above-mentioned cross-linking reagent, for example, has the aminooxy group, and
aldehyde groups in the sugar of the first nucleic acid strand and the second nucleic acid strand are linked via the aminooxy group of the cross-linking reagent in the cross-linked double-stranded nucleic acid.

The method of nucleic acid hybridization according to the second aspect of the present disclosure comprises
the step of hybridizing the nucleic acid complex according to the first aspect of the present disclosure with a target nucleic acid comprising a base sequence that is completely or sufficiently complementary to a base sequence of a single-stranded nucleic acid that forms the nucleic acid complex.

The pharmaceutical composition according to the third aspect of the present disclosure comprises
the nucleic acid complex according to the first aspect of the present disclosure.

The probe for nucleic acid detection according to the fourth aspect of the present disclosure comprises
the nucleic acid complex according to the first aspect of the present disclosure.

The complementary strand nucleic acid complex according to the fifth aspect of the present disclosure comprises
the first nucleic acid complex comprising the first single-stranded nucleic acid and the first cross-linked double-stranded nucleic acid linked to the 5' end or the 3' end of the first single-stranded nucleic acid and
the second nucleic acid complex comprising the second single-stranded nucleic acid comprising a base sequence that is completely or sufficiently complementary to the base sequence of the first single-stranded nucleic acid,
wherein the first single-stranded nucleic acid and the second single-stranded nucleic acid are hybridized.

The above-mentioned second nucleic acid complex, for example, comprises the second cross-linked double-stranded nucleic acid linked to the 3' end or the 5' end of the second single-stranded nucleic acid.

Advantageous Effects of Invention

According to the present disclosure, it is possible to provide nucleic acid complexes capable of stably hybridizing with a target nucleic acid, methods of nucleic acid hybridization, pharmaceutical compositions, probes for nucleic acid detection, and complementary strand nucleic acid complexes.

BRIEF DESCRIPTION OF DRAWINGS

FIG. 3 is a figure showing the base sequence of the nucleic acid complexes (DNAs) of the Examples 1 to 10 and the base sequence of the molecules (DNAs) of Comparative Examples 1 to 5;

FIG. 5 a figure showing the base sequences of the nucleic acid complexes (2'-OMe RNAs) of Examples 13 to 18 and the base sequence of the molecules (2'-OMe RNAs) of Comparative Examples 10 to 18;

FIG. 7A is a figure showing the results of electrophoresis carried out for the nucleic acid complexes of Examples 1 and 9; and FIG. 7B is a figure showing the results of electrophoresis carried out for the nucleic acid complexes of Examples 14 to 17;

FIG. 11A is a figure showing the result of measurement of miRNA-suppression activity for the nucleic acid complex of Example 14; FIG. 11B is a figure showing the result of measurement of miRNA-suppression activity for the nucleic acid complex of Example 15; FIG. 11C is a figure showing the result of measurement of miRNA-suppression activity for the nucleic acid complex of Example 17; and FIG. 11D is a figure showing the result of measurement of miRNA-suppression activity for the nucleic acid complex of Example 17;

FIG. 12A is a figure showing the base sequences of complementary strand nucleic acid complexes of Examples 19 (dc34dU: SEQ ID NO: 49; and d5'CL (12/34): SEQ ID NO: 3 and SEQ ID NO: 4) and 20 (dcCL (12/34): SEQ ID NO: 50 and SEQ ID NO: 51; and d5'CL (12/34): SEQ ID NO: 3 and SEQ ID NO: 4) and the base sequence of molecule of Comparative Example 19 (dc34dU 5' to 3': SEQ ID NO: 49; and d34dU 3' to 5': SEQ ID NO: 52); FIG. 12B is a figure showing schematically the complementary strand nucleic acid complex of Example 19; FIG. 12C is a figure showing schematically the complementary strand nucleic acid complex of Example 20; and FIG. 12D is a figure showing the results of Tm value measurement for the complementary strand nucleic acid complexes of Examples 19 and 20 and the molecule of Comparative Example 19;

DESCRIPTION OF EMBODIMENTS

Figure 1:
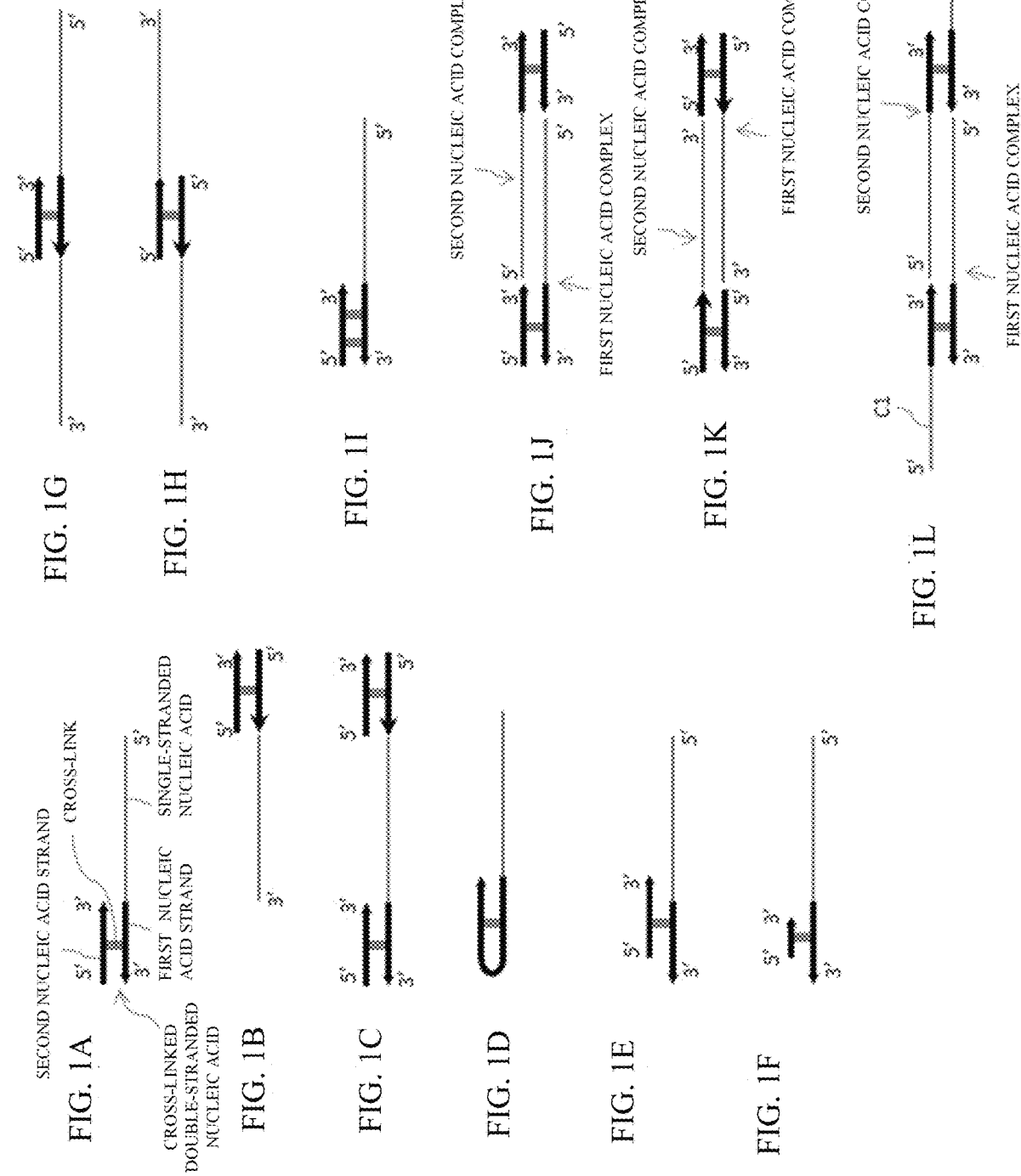
FIG. 1A is a figure showing schematically a nucleic acid complex having a cross-linked double-stranded nucleic acid linked to the 3' end of a single-stranded nucleic acid.
FIG. 1B is a figure showing schematically a nucleic acid complex having a cross-linked double-stranded nucleic acid linked to the 5' end of a single-stranded nucleic acid.
FIG. 1C is a figure showing schematically a nucleic acid complex having two cross-linked double-stranded nucleic acids linked to both of the 5' end and the 3' end of a single-stranded nucleic acid.
FIG. 1D is a figure showing schematically a nucleic acid complex having a cross-linked double-stranded nucleic acid with a hairpin loop structure.
FIG. 1E is a figure showing schematically a nucleic acid complex having a cross-linked double-stranded nucleic acid of an another aspect, which nucleic acid complex comprises the first nucleic acid strand and the second nucleic acid strand with the same length.
FIG. 1F is a figure showing schematically a nucleic acid complex having a cross-linked double-stranded nucleic acid of an another aspect, which nucleic acid complex comprises the first nucleic acid strand and the second nucleic acid strand with different lengths.
FIG. 1G is a figure showing schematically a nucleic acid complex with a single-stranded nucleic acid being linked to both of the 5' end and the 3' end of a first nucleic acid strand.
FIG. 1H is a figure showing schematically a nucleic acid complex with a single-stranded nucleic acid being linked to the 3' end of the first nucleic acid strand and further with a single-stranded nucleic acid being linked to the 3' end of the second nucleic acid strand.
FIG. 1I is a figure showing schematically a form in which two cross-linking sites are present.
FIG. 1J is a figure showing schematically a complementary strand nucleic acid complex having a cross-linked double-stranded nucleic acid with the first nucleic acid complex being linked to the 3' end of a single-stranded nucleic acid.
FIG. 1K is a figure showing schematically a complementary strand nucleic acid complex having a cross-linked double-stranded nucleic acid with the first nucleic acid complex being linked to the 5' end of a single-stranded nucleic acid.
FIG. 1L is a figure showing schematically a complementary strand nucleic acid complex that further has nucleic acid strand $C_1$ linked to the 5' end of the first cross-linked double-stranded nucleic acid and nucleic acid strand C2 linked to the 5' end of the second cross-linked double-stranded nucleic acid.

First, the nucleic acid complex according to the present disclosure will be described in detail.

The nucleic acid complex according to the present disclosure comprises
  a single-stranded nucleic acid and
  a cross-linked double-stranded nucleic acid comprising the first nucleic acid strand linked to at least one of the 5' end and the 3' end of the single-stranded nucleic acid and the second nucleic acid strand comprising a base sequence that is completely or sufficiently complementary to the first nucleic acid strand.

The term "single-stranded nucleic acid" described above refers to a "nucleic acid comprising a base sequence that is completely or sufficiently complementary to the base sequence of a target nucleic acid." In the present specification, the "single-stranded nucleic acid" may be DNA; RNA; a modified nucleic acid obtained by derivatization of a sugar moiety of nucleic acid such as 2'-O-methylated RNA (hereinafter referred to as 2'-OMe RNA) and locked nucleic acid (hereinafter referred to as LNA); a modified nucleic acid obtained by derivatization of a phosphodiester bond (for example, a phosphothioester bond in which an oxygen atom is replaced with a sulphur atom); other modified nucleic acids; or a mixture thereof. It is to be noted that these modified nucleic acids are disclosed in, for example, Deleavey, G. F. and Damha, M. J., Chemistry & Biology, 19, 937-954, 2012.

In the present specification, a "target nucleic acid" may be either DNA or RNA; and examples thereof can include non-coding RNA (microRNA, ribosomal RNA, tRNA, or the like), mRNA, and single-stranded DNA. The target nucleic acid may be those present within a living organism or those present outside of a living organism. The length of target nucleic acid is not particularly restricted and is, for example, preferably 5 to 30 mer and more preferably 10 to 25 mer.

In the present specification, "(a single-stranded nucleic acid) comprising a base sequence that is completely complementary (to the base sequence of a target nucleic acid)" means that the single-stranded nucleic acid comprises only a base sequence capable of pairing with all bases of the base sequence of a target nucleic acid.

In the present specification, "(a single-stranded nucleic acid) comprising a base sequence that is sufficiently complementary (to the base sequence of a target nucleic acid)" is those comprising a base sequence that can be paired with not less than 50% and less than 100%, preferably not less than 60% and less than 100%, more preferably not less than 70% and less than 100%, further preferably not less than 80% and less than 100%, still more preferably not less than 90% and less than 100% of bases in the base sequence of a target nucleic acid. To be specific, examples include cases where one or two to four bases in the nucleic acid strand comprising a base sequence that is completely complementary to the base sequence of a target nucleic acid are substituted with other bases and, as a result, nucleotide residues at the substitution positions become unable to make pairing (in these cases, the position at which the substitution with other bases takes place is referred to as a "mismatch site") and cases where one or two to four bases in the nucleic acid strand comprising a base sequence that is completely complementary to the base sequence of a target nucleic acid are deleted and, as a result, nucleotide residues at the deletion positions become unable to make pairing.

In the present specification, a "single-stranded nucleic acid comprising a base sequence that is completely complementary to the base sequence of a target nucleic acid" and a "single-stranded nucleic acid comprising a base sequence that is sufficiently complementary to the base sequence of a target nucleic acid" may in some cases be collectively referred to as simply a "single-stranded nucleic acid". It is to be noted that the "single-stranded nucleic acid" is shown using a lateral thin line in FIG. 1A to L.

Figure 15:
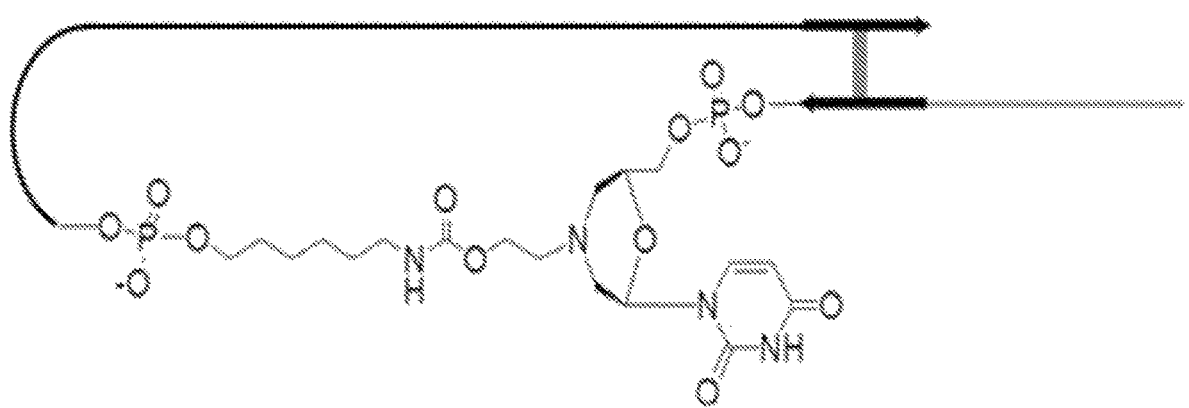
FIG. 15 is an example of a nucleotide or nucleotides+alkyl chain having 2 to 20 carbon atoms in this case (thymidine+alkyl chain).
Figure 16:
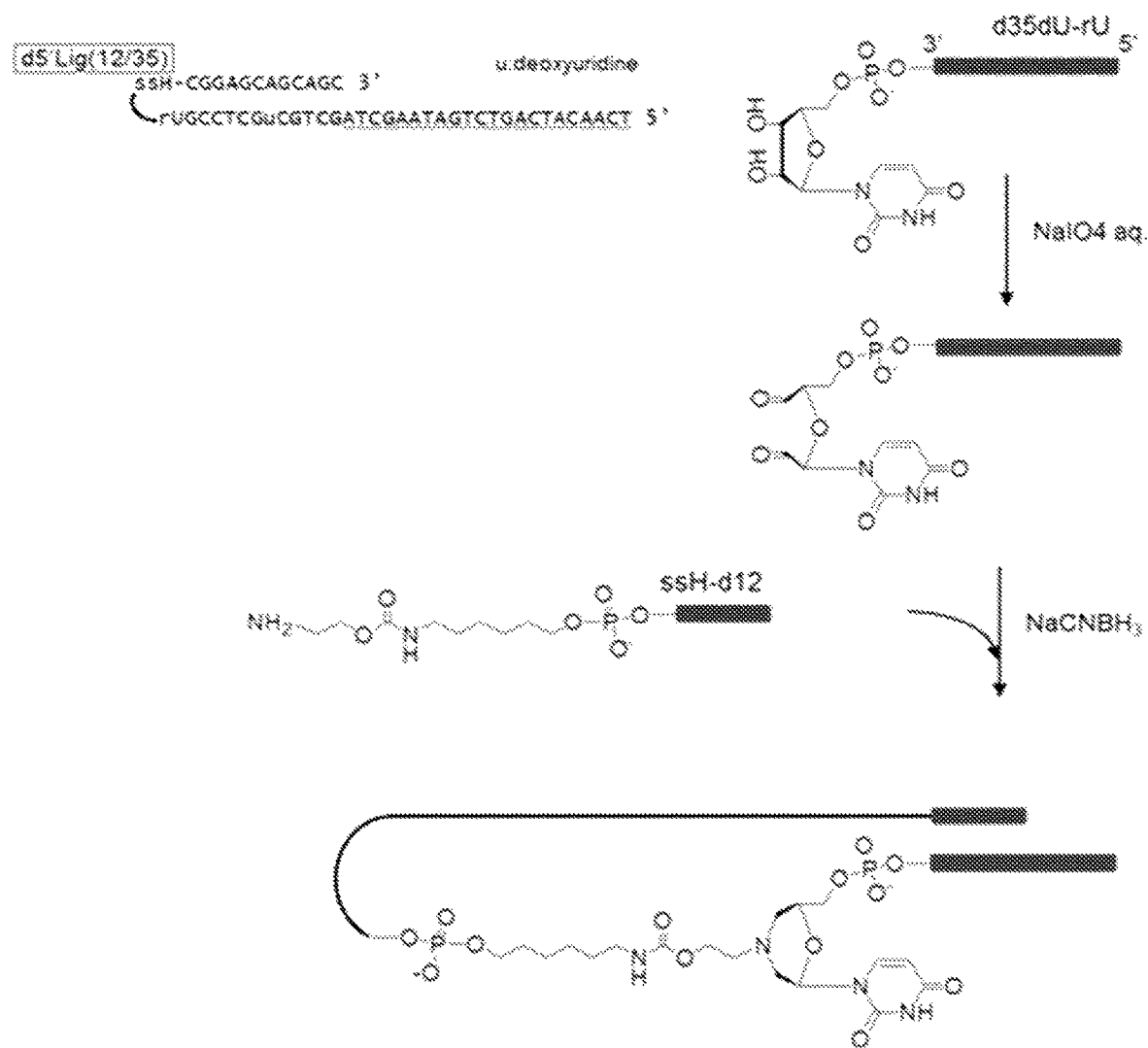
FIG. 16 is a synthesis scheme for d5'Lig(12/35) (Comparative Example 4).

The above-mentioned "cross-linked double-stranded nucleic acid" includes those comprising two nucleic acid strands comprising a completely or sufficiently complementary base sequence, which is linked to at least one of the 5' end and the 3' end of a single-stranded nucleic acid (the "cross-linked double-stranded nucleic acid" is indicated by two lateral bold arrows in FIG. 1). The "cross-linked double-stranded nucleic acid" comprises two nucleic acid strands; and one nucleic acid strand (the first nucleic acid strand) and the other nucleic acid strand (the second nucleic acid strand) comprising a base sequence that is completely or sufficiently complementary (in the same way as described above) to the nucleic acid strand (the first nucleic acid strand) are hybridized and, in addition, the first nucleic acid strand and the second nucleic acid strand are bound and cross-linked in the nucleic acid strand of the first nucleic acid strand and the second nucleic acid strand (in FIG. 1, the vertical wide line indicates that the first nucleic acid strand and the second nucleic acid strand are cross-linked). Here, the "cross-linked double-stranded nucleic acid" includes those in which two nucleic acid strands are linked via a hairpin loop structure outside of the nucleic acid strands (FIG. 1D). Examples of the link of the hairpin loop structure in this case include a polynucleotide (for example, a polynucleotide comprising 3 to 10 bases (for example, thymidine residues)); an alkyl chain having 2 to 20 carbon atoms; a polynucleotide (for example, 3 to 10 mer)+an alkyl chain having 2 to 20 carbon atoms; and a nucleotide or nucleotides+an alkyl chain having 2 to 20 carbon atoms. An example of "a nucleotide or nucleotides+alkyl chain having 2 to 20 carbon atoms" in this case (thymidine+alkyl chain) is shown in FIG. 15.

The two nucleic acid strands (that is, the first nucleic acid strand and the second nucleic acid strand) in the cross-linked double-stranded nucleic acid may be DNA; RNA; a modified nucleic acid obtained by derivatization of a sugar moiety of a nucleic acid such as 2'-OMe RNA and LNA; a modified nucleic acid obtained by derivatization of a phosphodiester bond; other modified nucleic acids; or a mixture thereof. It is to be noted that these modified nucleic acids are the same as described above. Further, the length of the first nucleic acid strand and the second nucleic acid strand is not particularly restricted and is, for example, preferably 5 bp to 30 bp, more preferably 7 bp to 20 bp, and still more preferably 9 bp to 12 bp. Further, the first nucleic acid strand and the second nucleic acid strand may have the same lengths or may have different lengths. In the case in which the length of the first nucleic acid strand and the second nucleic acid strand is the same, besides the mode shown in FIG. 1A to C, what is also includes is, for example, as shown in FIG. 1E, a mode in which a sequence part that is not completely or sufficiently complementary to the second nucleic acid strand is present at the 3' side of the first nucleic acid strand and, at the same time, a sequence part that is not completely or sufficiently complementary to the first nucleic acid strand is present at the 3' side of the second nucleic acid strand. Further, examples of cases where the first nucleic acid strand and the second nucleic acid strand have different lengths include a mode in which, as shown in FIG. 1F, the first nucleic acid strand is longer than the second nucleic acid strand and a sequence part that is not completely or sufficiently complementary to the second nucleic acid strand is present at both of the 5' side and the 3' side of the first nucleic acid strand. Further, whereas the single-stranded nucleic acid is linked to the 5' end of the first nucleic acid strand of the cross-linked double-stranded nucleic acid in FIG. 1A and the single-stranded nucleic acid is linked to the 3' end of the first nucleic acid strand in FIG. 1B, the single-stranded nucleic acid may be, as shown in FIG. 1G, linked to both of the 5' end and the 3' end of the first nucleic acid strand. Further, as shown in FIG. 1H, the single-stranded nucleic acid may be linked to the 3' end of the first nucleic acid strand and the single-stranded nucleic acid may be further the 3' end of the second nucleic acid strand. (Similarly, the single-stranded nucleic acid may be linked to the 5' end of the first nucleic acid strand and the single-stranded nucleic acid may be further the 5' end of the second nucleic acid strand.)

Further, the cross-linked double-stranded nucleic acid may be, as shown in FIG. 1A, linked to the 3' end of the single-stranded nucleic acid or may be, as shown in FIG. 1B, linked to the 5' end of the single-stranded nucleic acid. Preferably, the cross-linked double-stranded nucleic acid is, as shown in FIG. 1B, linked to the 5' end of single-stranded nucleic acid. The cross-linking between the nucleic acid strands of the first nucleic acid strand and the second nucleic acid strand makes it possible to reduce dissociation between the nucleic acid strands of the first nucleic acid strand and the second nucleic acid strand in the cross-linked double-stranded nucleic acid and to keep the single-stranded nucleic acid and a target nucleic acid hybridized stably. It is to be noted that, in the present specification, the "cross-linked double-stranded nucleic acid" may in some cases be referred to as a "cross-linking adapter sequence".

It is to be noted that the "single-stranded nucleic acid" and the "cross-linked double-stranded nucleic acid" in the nucleic acid complex according to the present disclosure may be the same kind or different kinds of nucleic acids. For example, the "single-stranded nucleic acid" may be RNA and the "cross-linked double-stranded nucleic acid" may be DNA.

In the cross-linked double-stranded nucleic acid, two nucleic acid strands of the first nucleic acid strand and the second nucleic acid strand are bound and cross-linked; and a method of cross-linking is not particularly restricted and any can be as appropriate employed as long as it is a technique capable of linking the two nucleic acid strands of the first nucleic acid strand and the second nucleic acid strand. The two nucleic acid strands of the first nucleic acid strand and the second nucleic acid strand may be cross-linked by, for example, a bond via a sugar of at least one of the first nucleic acid strand and the second nucleic acid strand. Further, the two nucleic acid strands of the first nucleic acid strand and the second nucleic acid strand may be cross-linked by, for example, a bond between sugars of the first nucleic acid strand and the second nucleic acid strand; and in this case the sugars of the first nucleic acid strand and the second nucleic acid strand may be bound by a covalent bond including an amide bond, an oxime bond, an alkylamide bond, an S—S bond, and a carbon-carbon bond (for example, a bond via an alkyl chain having 2 to 10 carbon atoms).

In the case in which the first nucleic acid strand and the second nucleic acid strand are cross-linked between sugars thereof in the cross-linked double-stranded nucleic acid, a reactive group present in the sugar of the nucleic acid or a reactive group introduced to the sugar of the nucleic acid may, for example, be linked by a cross-linking reagent. Examples of the reactive group in this case can include an aldehyde group, a thiol group, an azide group, and an amino group.

The sugars in the nucleic acid strand of the first nucleic acid strand and the second nucleic acid strand may be linked by a cross-linking reagent having, for example, an aminooxy group or an amino group. In this case, the reactive groups of the sugars are linked by reacting a reactive group of the sugar (for example, an aldehyde group, a thiol group, an azide group, an amino group, or the like) with the aminooxy group or the amino group.

Examples of the cross-linking reagent with an aminooxy group or an amino group can include a compound represented by general formula 1:

R₁—NH—O-L₁-D-L₂-A    (1)

(wherein
R₁ is a protective group of a hydrogen atom, an alkyl group, or an amino group,
D is an aromatic group selected from a substituted or unsubstituted phenylene group, a substituted or unsubstituted anthrylene group, a substituted or unsubstituted naphthylene group, a substituted or unsubstituted phenanthrylene group, a substituted or unsubstituted anthraquinolylene group, and a substituted or unsubstituted acridinylene group, or a $C_{2-10}$ alkyl group,
a substituent of the aromatic group is selected from the group consisting of a halogen atom, a $C_{1-6}$ alkyl group, a nitro group, a cyano group, a $C_{2-6}$ alkenyl group, a $C_{3-10}$ cycloalkyl group, a $C_{1-10}$ alkoxy group, and a $C_{1-10}$ acyl group, L₁ is a direct bond or a divalent group represented by the following general formula 3 or 4:

(3)

(4)

(wherein R₃ is a $C_{1-9}$ alkylene group or —$(CH_2)_o$—$(OCH_2CH_2)_p$—$(CH_2)_q$—, o to q are each independently an integer of 0 to 15, o+p+q is 1 to 15), L₂ is a direct bond or a divalent group represented by the following general formula 5 or 6:

(5)

(6)

(wherein R₄ is a $C_{1-9}$ alkylene group or —$(CH_2)_r$—$(OCH_2CH_2)_s$—$(CH_2)_t$—, r to t are each independently an integer of 0 to 15, r+s+t is 1 to 15), and A is an aminooxy group or a protected aminooxy group) or a salt thereof. This cross-linking reagent is as described in Japanese Patent No. 5196448.

In the cross-linked double-stranded nucleic acid, aldehyde groups in the sugars of the first nucleic acid strand and the second nucleic acid strand may be linked via an aminooxy group (divalent) of a cross-linking reagent. In this case, a cross-linking reagent having an aminooxy group is used; and $N^1,N^5$-bis(aminooxyacetyl)-1,5-diaminonaphthalene (aoNao) which is shown below may, for example, be used as the cross-linking reagent.

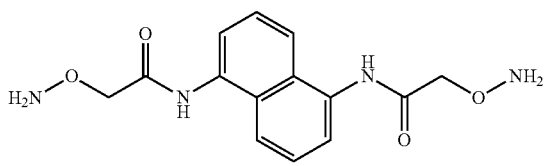 [SMILES: NOCC(=O)Nc1cccc2c(NC(=O)CON)cccc12]

Figure 6A:
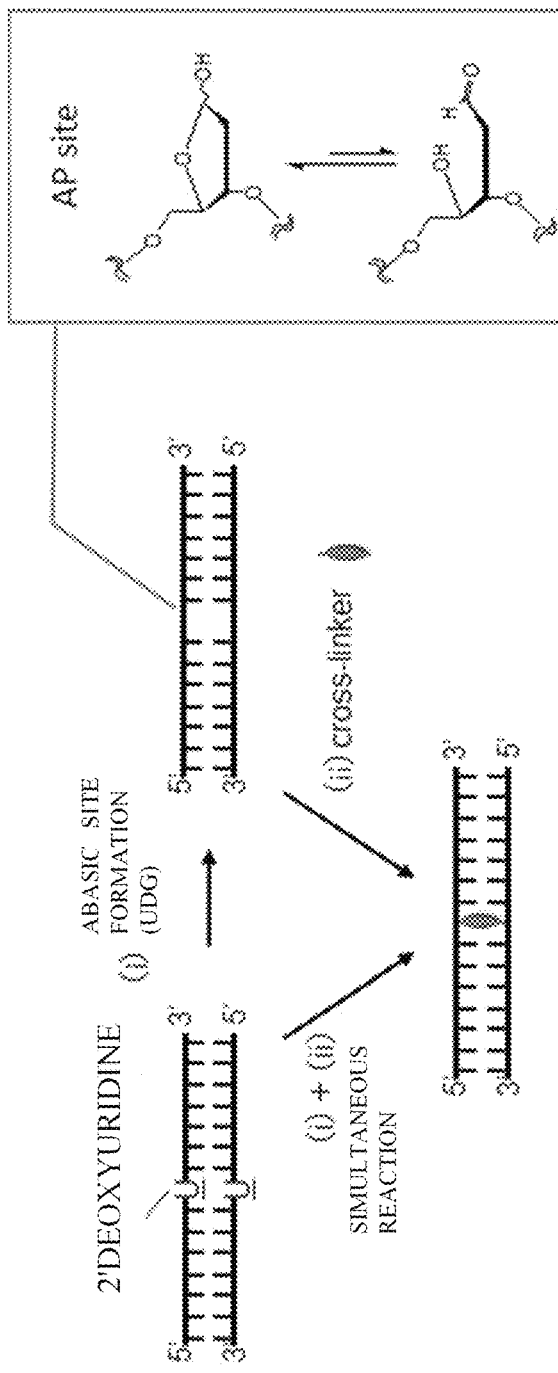
FIG. 6A is a figure illustrating the step of binding aldehyde groups in sugars of the first nucleic acid strand and the second nucleic acid strand in a cross-linked double-stranded nucleic acid via a cross-linking reagent.

In the cross-linked double-stranded nucleic acid, in the case in which the aldehyde groups of the sugars of the first nucleic acid strand and the second nucleic acid strand are linked via the aminooxy group (divalent) of the cross-linking reagent, an example method is a method comprising synthesizing the first nucleic acid strand and the second nucleic acid strand so as to contain deoxyuridine at a position at which the first nucleic acid strand and the second nucleic acid strand make pairing; treating the first nucleic acid strand and the second nucleic acid strand with Uracil DNA glycosylase (UDG) to allow an AP site to be formed in the deoxyuridine of the first nucleic acid strand and the second nucleic acid strand (FIG. 6A (i)) (the AP site exists in an equilibrium state; and an open ring form has an aldehyde group); and adding a cross-linking reagent thereto to bring into ligation reaction with the aldehyde group, thereby cross-linking the first nucleic acid strand and the second nucleic acid strand (FIG. 6A (ii)).

The two nucleic acid strands of the first nucleic acid strand and the second nucleic acid strand may be cross-linked via, for example, a bond via a sugar of at least one of the first nucleic acid strand and the second nucleic acid strand and may be cross-linked by, for example, a bond between the sugar and the base of the two nucleic acid strands. As for the bond between the sugar and the base of the two nucleic acid strands of the first nucleic acid strand and the second nucleic acid strand, an example method is a method comprising treating, with Uracil DNA glycosylase (UDG), the first nucleic acid strand or the second nucleic acid strand synthesized so as to contain deoxyuridine allow an AP site to be form at the deoxyuridine in the first nucleic acid strand or the second nucleic acid strand; and reacting —NH group of guanine or adenine of the second nucleic acid strand or the first nucleic acid strand with the aldehyde group of the AP site formed in the first nucleic acid strand or the second nucleic acid strand, thereby cross-linking the first nucleic acid strand and the second nucleic acid strand.

It is to be noted that, although FIG. 1A to C illustrate cross-linked double-stranded nucleic acids in which the nucleic acid strands of the first nucleic acid strand and the second nucleic acid strand are cross-linked only at one site, the nucleic acid strands of the first nucleic acid strand and the second nucleic acid strand may be cross-linked at two sites or three or more sites (FIG. 1I shows a mode with two cross-linking sites). The more increased number of the sites at which the nucleic acid strands of the first nucleic acid strand and the second nucleic acid strand are cross-linked increases allows less dissociation of the nucleic acid strands of the first nucleic acid strand and the second nucleic acid strand in the cross-linked double-stranded nucleic acid. It is to be noted that in cases where the nucleic acid strands of the first nucleic acid strand and the second nucleic acid strand are cross-linked at, for example, two sites or three or more sites, each of the sites may be held by different types of bonds may different from each site (for example, in the case of the two sites, one of the sites may be cross-linked by, for example, an amide bond whereas the other site may be cross-linked by, for example, an oxime bond; and different cross-linking reagents may, for example, be used from one site to the other site.) Further, with regard to the site at which the nucleic acid strands of the first nucleic acid strand and the second nucleic acid strand are cross-linked, in the case in which 12-mer nucleic acid strands are, for example, cross-linked at one site to form a cross-linked double-stranded nucleic acid, the 12-mer nucleic acid strands may be bound and cross-linked at a site located at a substantially center (the sixth or seventh nucleic acid from the 5' end).

In the nucleic acid complex according to the present disclosure, the cross-linked double-stranded nucleic acid is linked to at least one of the 5' end and the 3' end of a single-stranded nucleic acid. That is, one cross-linked double-stranded nucleic acid may be linked to the 3' end of the single-stranded nucleic acid (FIG. 1A); one cross-linked double-stranded nucleic acid may be linked to the 5' end of the single-stranded nucleic acid (FIG. 1B); or one cross-linked double-stranded nucleic acid may be linked to each of both 5' end and 3' end of the single-stranded nucleic acid (FIG. 1C). In the case in which one cross-linked double-stranded nucleic acid is linked to each of both 5' end and 3' end of the single-stranded nucleic acid (FIG. 1C), the base sequences of the two cross-linked double-stranded nucleic acids may be the same or different. It is to be noted that, as just described above, the cross-linked double-stranded nucleic acid may be linked to the 3' end of the single-stranded nucleic acid as shown in FIG. 1A or may be linked to the 5' end of the single-stranded nucleic acid as shown in FIG. 1B and is preferably linked to the 5' end of the single-stranded nucleic acid as shown in FIG. 1B.

Means for linking the cross-linked double-stranded nucleic acid to the single-stranded nucleic acid is not particularly limited. In cases where the cross-linked double-stranded nucleic acid is linked to, for example, the 5' end of the single-stranded nucleic acid, the nucleoside of the 5' end of the single-stranded nucleic acid form a phosphodiester bond to be linked with the nucleoside of the 3' end of one nucleic acid strand of the cross-linked double-stranded nucleic acid. In cases where the cross-linked double-stranded nucleic acid is linked to, for example, the 3' end of the single-stranded nucleic acid, the nucleoside of the 3' end of the single-stranded nucleic acid form a phosphodiester bond to be linked with the nucleoside of the 5' end of one nucleic acid strand of the cross-linked double-stranded nucleic acid. Further, a "linker (spacer)" may be inserted between the single-stranded nucleic acid and one of the nucleic acid strands of the cross-linked double-stranded nucleic acid. In the present specification, the "linker (spacer)" may be, for example, one nucleotide (for example, guanine or the like) or a 2- to 20-mer polynucleotide (for example, several thymidine residues, GCC, or the like), or may be a linear alkyl chain having 1 to 20 carbon atoms. A propyl linker is shown below as an example of the "linear alkyl chain having 1 to 20 carbon atoms" in this case.

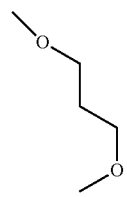

P: propyl linker

It is to be noted that he linker (spacer) described just above may be inserted or may not be inserted between the single-stranded nucleic acid and one of the nucleic acid strands of the cross-linked double-stranded nucleic acid.

An example of a method of synthesizing a nucleic acid complex (a nucleic acid complex in which both single-stranded nucleic acid and cross-linked double-stranded nucleic acid make of DNA) will be described. The first nucleic acid strand of the cross-linked double-stranded nucleic acid and an oligonucleotide having a base sequence of both of the second nucleic acid strand of the cross-linked double-stranded nucleic acid and a single-stranded nucleic acid, both strands being linked, are each synthesized by an automated DNA synthesizer (the first nucleic acid strand and the second nucleic acid strand are synthesized so as to contain deoxyuridine at a position at which the first nucleic acid strand and the second nucleic acid strand make pairing) and purified by a known method. The thus synthesized two kinds of DNA strands are placed in a solution containing Uracil DNA glycosylase (UDG) and reacted with the enzyme. To the obtained reaction solution, UDG is added for further reaction. To the obtained reaction solution, aoNao was added as a cross-linking reagent to allow for a reaction, thereby forming the cross-linked double-stranded nucleic acid. Purification is then carried out by HPLC to obtain the nucleic acid complex comprising DNA.

As described thus far, when the nucleic acid complex according to the present disclosure is hybridized with a target nucleic acid, the stability of hybridization between the target nucleic acid and the single-stranded nucleic acid in the nucleic acid complex is enhanced. Without wishing to be bound by a particular theory, this is thought to be because the structure of the cross-linked double-stranded nucleic acid becomes highly rigid due to the cross-linking in the nucleic acid complex according to the present disclosure and restricts physical movement, resulting in stable hybridization (between the target nucleic acid and the single-stranded nucleic acid) in adjacent sites. It is to be noted that, as described later in Examples, in the case in which one cross-linked double-stranded nucleic acid is linked to each of both 5' end and 3' end of the single-stranded nucleic acid (FIG. 1C), the stability of hybridization between the target nucleic acid and the single-stranded nucleic acid in the nucleic acid complex is more enhanced because a structurally stable cross-linked double-stranded nucleic acid is present at both ends.

Further because the cross-linked double-stranded nucleic acids exhibits a very high resistance to nucleases, the nucleic acid complex according to the present disclosure is able to continuously produce the effect within a living organism.

Further, according to the nucleic acid complex according to the present disclosure, because stable hybridization is feasible without chemical modification for stabilizing a target nucleic acid and a single-stranded nucleic acid hybridizing therewith, the cost of synthesis can be reduced.

Next, the method of nucleic acid hybridization according to the present disclosure will be described.

The method of nucleic acid hybridization according to the present disclosure comprises the step of hybridizing the nucleic acid complex described above with a target nucleic acid comprising a base sequence that is completely or sufficiently complementary (in the same way as described above) to the base sequence of the single-stranded nucleic acid (as described above) composing the nucleic acid complex. The step of "hybridizing the nucleic acid complex with a target nucleic acid" include, for example, introducing the nucleic acid complex to a living organism to hybridize with a target nucleic acid present within a living organism; adding the nucleic acid complex to a solution containing a target nucleic acid to hybridize with the target nucleic acid; bringing the nucleic acid complex into contact with a solid phase on which a target nucleic acid is supported to hybridize with the target nucleic acid; or the like. According to the method of nucleic acid hybridization according to the present disclosure, the stability of hybridization between the target nucleic acid and the single-stranded nucleic acid in the nucleic acid complex is enhanced.

Next, the pharmaceutical composition according to the present disclosure will be described.

The pharmaceutical composition according to the present disclosure contains the nucleic acid complex described above and can be used as an antisense nucleic acid pharmaceutical product targeting non-coding RNA (microRNA, Ribosomal RNA, tRNA, or the like), mRNA, single-stranded DNA, or the like which is present within a living organism. To be more specific, the entire sequence or a partial sequence of non-coding RNA (microRNA, Ribosomal RNA, tRNA, or the like), mRNA, single-stranded DNA, or the like which is present within a living organism is regarded as the "target nucleic acid"; and a nucleic acid complex containing a single-stranded nucleic acid comprising a base sequence that is completely or sufficiently complementary (in the same way as described above) to the base sequence of the target nucleic acid can be used as an antisense nucleic acid pharmaceutical product.

The pharmaceutical composition according to the present disclosure can for example be used as a microRNA inhibitor. In this case, the entire sequence or a partial sequence of microRNA present within a living organism is regarded as the "target nucleic acid". Examples of the microRNA can include miRNA21, miRNA122, miRNA224, miRNA10b, miRNA221, miRNA222, miRNA20, miRNA18, miRNA23a, miRNA141, miRNA200b, miRNA27a, miRNA342, miRNA26a, miRNA30d, miRNA26b, miRNA107, miRNA203, miRNA204, miRNA211, miRNA105, miRNA181a, miRNA155, miRNA181b, miRNA25, miRNA424, miRNA151, miRNA223, miRNA25, miRNA17-5p, miRNA125b, miRNA106a, miRNA92, miRNA103, miRNA93, miRNA100, miRNA106b, miRNA20a, miRNA190, miRNA33, miRNA19a, miRNA140, miRNA123, miRNA188, miRNA154, miRNA217, miRNA101, miRNA196, miRNA134, miRNA132, miRNA192, miRNA16, miRNA15, miRNA200a, miRNA200c, miRNA191, miRNA210, miRNA32, miRNA182, miRNA31, and miRNA146a.

The pharmaceutical composition according to the present disclosure can, for example, be used to directly control mRNA. In this case, the entire sequence or a partial sequence of mRNA present within a living organism is regarded as the "target nucleic acid".

Because the pharmaceutical composition according to the present disclosure contains the nucleic acid complex, it is able to enhance stable hybridization between the target nucleic acid and the single-stranded nucleic acid in the nucleic acid complex and to be thus highly effective as a pharmaceutical product. In addition, because the pharmaceutical composition is able to stably hybridize with the target nucleic acid, the amount of pharmaceutical composition to be administered is expected to be reduced.

Next, the probe for nucleic acid detection according to the present disclosure will be described.

The probe for nucleic acid detection according to the present disclosure contains the nucleic acid complex described above and can be used as a probe for nucleic acid detection targeting non-coding RNA (microRNA, Ribosomal RNA, tRNA, or the like), mRNA, single-stranded DNA, or the like which is present within or outside of a living organism. To be specific, the entire sequence or a partial sequence of non-coding RNA (microRNA, Ribosomal RNA, tRNA, or the like), mRNA, single-stranded DNA, or the like which is present within or outside of a living organism is regarded as the "target nucleic acid"; and a nucleic acid complex containing a single-stranded nucleic acid comprising a base sequence that is completely or sufficiently complementary (in the same way as described above) to the base sequence of the target nucleic acid can be used as a probe for nucleic acid detection. In order to detect the hybridization with the target nucleic acid, the nucleic acid complex may be labeled with a fluorescent substance.

Because the probe for nucleic acid detection according to the present disclosure contains the nucleic acid complex described above, enhanced stability of the hybridization between the target nucleic acid and the single-stranded nucleic acid in the nucleic acid complex can be attained, allowing highly sensitive detection of nucleic acids.

Next, the complementary strand nucleic acid complex according to the present disclosure will be described.

The complementary strand nucleic acid complex according to the present disclosure comprises
- the first nucleic acid complex containing the first single-stranded nucleic acid and the first cross-linked double-stranded nucleic acid linked to the 5' end or the 3' end of the first single-stranded nucleic acid, and
- the second nucleic acid complex containing the second single-stranded nucleic acid comprising a base sequence that is completely or sufficiently complementary to the base sequence of the first single-stranded nucleic acid,
- wherein the first single-stranded nucleic acid and the second single-stranded nucleic acid are hybridized.

In the complementary strand nucleic acid complex according to the present disclosure, the second nucleic acid complex may, for example, contain the second cross-linked double-stranded nucleic acid linked to the 3' end or the 5' end of the second single-stranded nucleic acid. In this case, both of the first nucleic acid complex and the second nucleic acid complex have the cross-linked double-stranded nucleic acid. It is to be noted that the first cross-linked double-stranded nucleic acid and the second cross-linked double-stranded nucleic acid may have a hairpin loop structure as shown in FIG. 1D.

FIG. 1J shows a schematic view of the first form of the complementary strand nucleic acid complex in the case in which both of the first nucleic acid complex and the second nucleic acid complex have the cross-linked double-stranded nucleic acid. In the first form of the complementary strand nucleic acid complex, the first nucleic acid complex has the first cross-linked double-stranded nucleic acid linked to the 3' end of the first single-stranded nucleic acid and the second nucleic acid complex has the second cross-linked double-stranded nucleic acid linked to the 3' end of the second single-stranded nucleic acid, wherein the first single-stranded nucleic acid and the second single-stranded nucleic acid are hybridized.

FIG. 1K shows a schematic view of the second form of the complementary strand nucleic acid complex in the case in which both of the first nucleic acid complex and the second nucleic acid complex have the cross-linked double-stranded nucleic acid. In the first form of the complementary strand nucleic acid complex, the first nucleic acid complex has the first cross-linked double-stranded nucleic acid linked to the 5' end of the first single-stranded nucleic acid and the second nucleic acid complex has the second cross-linked double-stranded nucleic acid linked to the 5' end of the second single-stranded nucleic acid, wherein the first single-stranded nucleic acid and the second single-stranded nucleic acid are hybridized.

It is to be noted that, in the case in which both of the first nucleic acid complex and the second nucleic acid complex have the cross-linked double-stranded nucleic acid, the first cross-linked double-stranded nucleic acid and the second cross-linked double-stranded nucleic acid may have the same base sequence or may have different base sequences in each of the first form of the complementary strand nucleic acid complex and the second form of the complementary strand nucleic acid complex.

Because the complementary strand nucleic acid complex according to the present disclosure has the first cross-linked double-stranded nucleic acid or both of the first cross-linked double-stranded nucleic acid and the second cross-linked double-stranded nucleic acid, stable hybridization as double strands can be achieved.

It is to be noted that the complementary strand nucleic acid complex according to the present disclosure may further have, for example, nucleic acid strand $C_1$ linked to the 5' end of the first cross-linked double-stranded nucleic acid and nucleic acid strand C2 linked to the 5' end of the second cross-linked double-stranded nucleic acid, as shown in FIG. 1L. The base sequence of the nucleic acid strand C1 is a base sequence that is completely or sufficiently complementary (in the same way as described above) to the base sequence of the nucleic acid strand C2; and the nucleic acid strand C1 and the nucleic acid strand C2 are able to stably hybridized. Having the nucleic acid strand C1 and the nucleic acid strand C2 may allow a stable polymerized structure with a chain of two or more molecules. It is to be noted that the complementary strand nucleic acid complex according to other aspects may be a complementary strand nucleic acid complex that further has the nucleic acid strand C1 linked to the 3' end of the first cross-linked double-stranded nucleic acid and the nucleic acid strand C2 linked to the 3' end of the second cross-linked double-stranded nucleic acid (the nucleic acid strand C1 and the nucleic acid strand C2 are the same as described above).

EXAMPLES

By way of example, the present disclosure will now be specifically described below. The present disclosure is, however, not limited to these examples.

Example A (Outline of Oligonucleotides Synthesized)

As target nucleic acids (target RNAs), miR21 (SEQ ID NO: 1) and miR21-M (miR21 with one base mismatch) (SEQ ID NO: 2) (both have 22 mer) were selected; and an oligonucleotide complementary to miR21 or miR21-M was synthesized.

The base sequences of miR21 and miR21-M are shown below.

```
miR21:
                              (SEQ ID NO: 1)
5' UAGCUUAUCAGACUGAUGUUGA 3' miR21-M:
                              (SEQ ID NO: 2)
5' UAGCUUAUCACACUGAUGUUGA 3'
```

Figure 2:
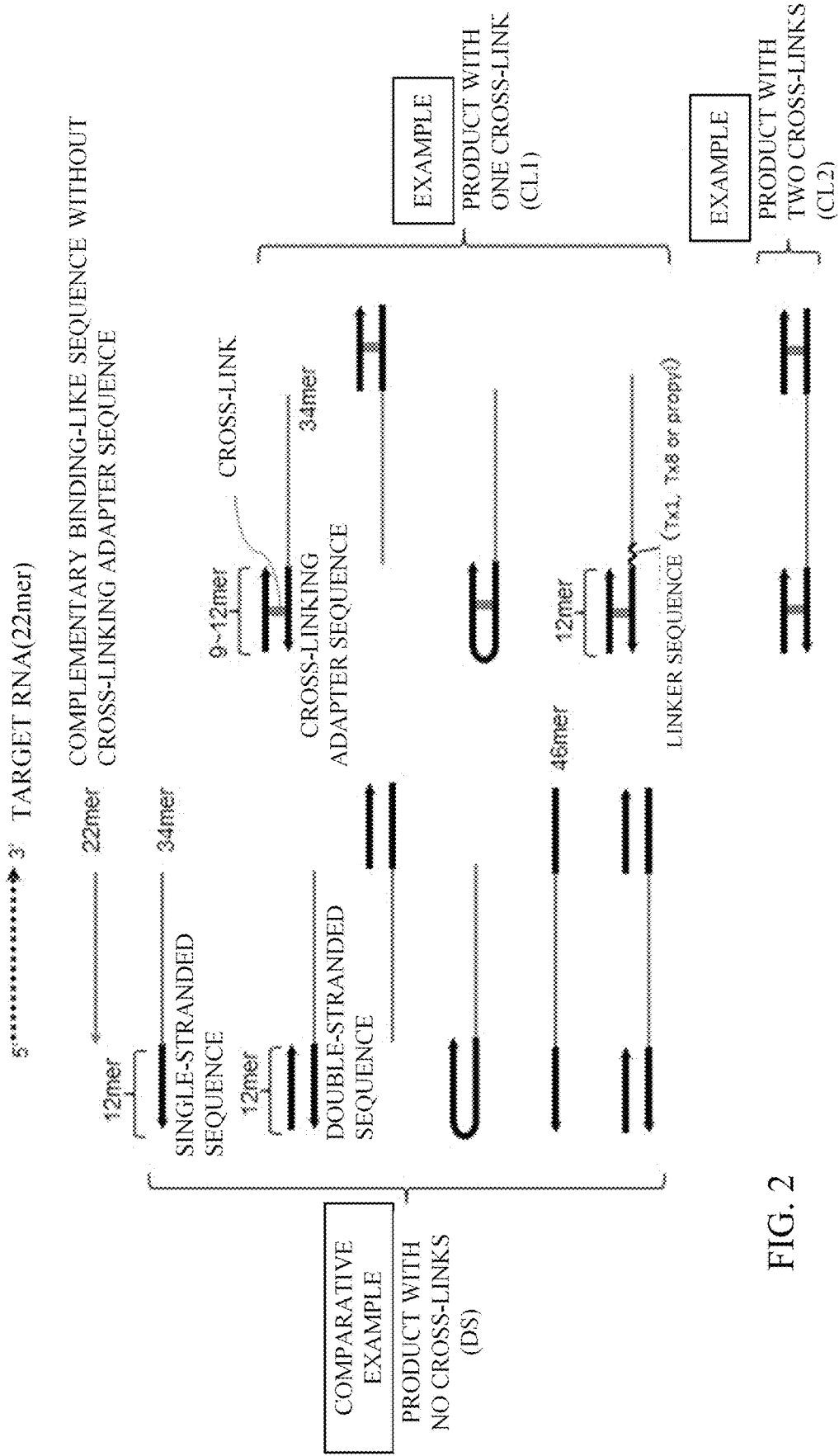
FIG. 2 is a figure showing schematically nucleic acid complexes (products with one cross-link and a product with two cross-links) of Examples and molecules (products with no cross-links) of Comparative Examples.

To be more specific with regard to the oligonucleotide complementary to miR21 or miR21-M, products with one cross-link (CL1) having a single-stranded nucleic acid comprising a base sequence that is completely or sufficiently complementary to the base sequence of a target nucleic acid (hereinafter referred to simply as a "complementary binding-like sequence" in the present Examples) and a double-stranded cross-linking adapter sequence at the 5' side or the 3' side (including those having the cross-linking adapter sequence with a hairpin loop structure and those having a linker inserted between the cross-linking adapter sequence and the complementary binding-like sequence); and products with two cross-links (CL2) having the complementary binding-like sequence and a double-stranded cross-linking adapter sequence at both of the 5' side and the 3' side were, as shown in FIG. 2, synthesized as Examples. In addition, products with no cross-links (DS) having a single-stranded nucleic acid strand comprising a base sequence complementary to the base sequence of a target RNA (hereinafter, referred to simply as a "complementary binding-like sequence" in the Examples) and a single-stranded nucleic acid strand linked to the complementary binding-like sequence (hereinafter, referred to simply as a "single-stranded adapter sequence" in the Examples) at the 5' side; products with no cross-links (DS) having the complementary binding-like sequence and a double-stranded nucleic acid strand linked to the complementary binding-like sequence (hereinafter, referred to simply as a "double-stranded adapter sequence" in the Examples) at the 5' side or the 3' side (including those with a double-stranded adapter sequence having a hairpin loop structure); products with no cross-links (DS) having the complementary binding-like sequence and the single-stranded adapter sequence at both of the 5' side and the 3' side; and products with no cross-links (DS) having the complementary binding-like sequence and the double-stranded adapter sequence at both of the 5' side and the 3' side were, as shown in FIG. 2, synthesized as Comparative Examples. In addition, a nucleic acid strand was synthesized as a control (Comparative Example), which nucleic acid strand did not have the cross-linking adapter sequence and have only the complementary binding-like sequence. Note that Comparative Example 18 (mCL2(12–I×2/34)) (FIG. 5) is an exception and is a Comparative Example in which the nucleic acid strand has the cross-linking adapter sequence but the length of a region hybridizing with miR21 is about 10 bases. It is to be noted that the direction of the arrow indicates from 5' to 3' in FIG. 2.

As for the oligonucleotides synthesized, the sequence of DNA (FIG. 3), RNA (FIG. 4), and 2'-O-methyl (2'-OMe) RNA (FIG. 5) is shown in each figure. Each of the oligonucleotides will be described below. It is to be noted that, in the Examples, the double-stranded cross-linking adapter sequence is cross-linked by a bond between sugars of two nucleic acid strands (FIG. 6A, described later).

(DNAs Synthesized)

Figure 3:
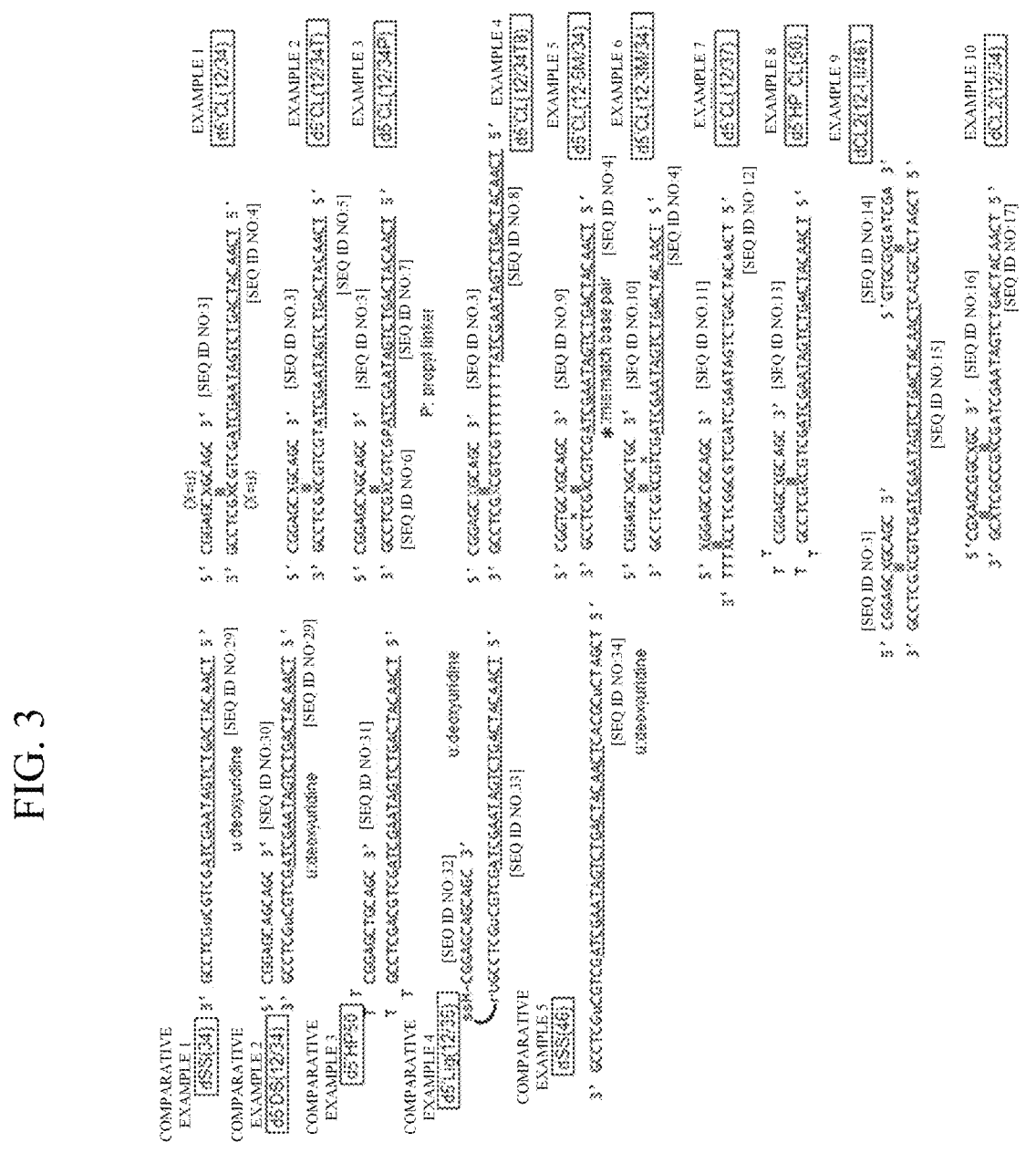

The sequences of DNAs synthesized are shown in FIG. 3. In FIG. 3, the sequence complementary to miR21 is underlined; "X" in the sequence represents a cross-linking site in the oligonucleotide chain; and the vertical wide line indicates that the nucleic acid strands are together cross-linked by a cross-linking reagent. It is to be noted that "u" represents deoxyuridine in FIGS. 3 to 5. The structural formula of deoxyuridine is shown below.

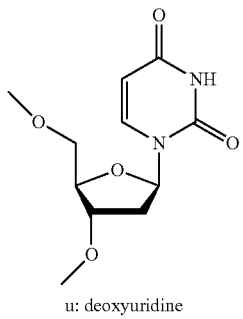

u: deoxyuridine

As Example 1, d5'CL(12/34) having a sequence complementary to miR21 (a complementary binding-like sequence) and a 12-mer double-stranded cross-linking adapter sequence was synthesized (FIG. 3).

As Example 2, d5'CL(12/34T) having a sequence complementary to miR21 (a complementary binding-like sequence) and a 12-mer double-stranded cross-linking adapter sequence with T (thymidine) as a linker therebetween was synthesized (FIG. 3).

As Example 3, d5'CL(12/34P) having a sequence complementary to miR21 (a complementary binding-like sequence) and a 12-mer double-stranded cross-linking adapter sequence with a propyl linker of the following formula therebetween was synthesized (FIG. 3).

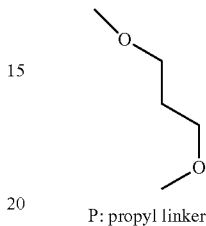

P: propyl linker

As Example 4, d5'CL(12/34T8) having a sequence complementary to miR21 (a complementary binding-like sequence) and a 12-mer double-stranded cross-linking adapter sequence with eight T (thymidine) residues as a linker therebetween was synthesized (FIG. 3).

As Example 5, d5'CL(12-5M/34) having a sequence complementary to miR21 (a complementary binding-like sequence) and a 12-mer double-stranded cross-linking adapter sequence with a mismatched base pair in the 5' side of the cross-linking site was synthesized (FIG. 3).

As Example 6, d5'CL(12-3M/34) having a sequence complementary to miR21 (a complementary binding-like sequence) and a 12-mer double-stranded cross-linking adapter sequence with a mismatched base pair in the 3' side of the cross-linking site was synthesized (FIG. 3).

As Example 7, d5'CL(12/37) having a sequence complementary to miR21 (a complementary binding-like sequence) and a 12-mer double-stranded cross-linking adapter sequence (the terminal site of the cross-linking adapter sequence was cross-linked and three thymidine residues were linked to the end of the cross-linking adapter sequence) was synthesized (FIG. 3).

As Example 8, d5'HP CL(50) having a sequence complementary to miR21 (a complementary binding-like sequence) and a 12-mer double-stranded cross-linking adapter sequence (having a hairpin loop structure comprising four thymidine residues) in the 3' side of the cross-linking site was synthesized (FIG. 3).

As Example 9, dCL2(12-I,II/46) having a sequence complementary to miR21 (a complementary binding-like sequence) and a 12-mer double-stranded cross-linking adapter sequence at both ends was synthesized (FIG. 3).

As Example 10, dCL2 (12/34) having a sequence complementary to miR21 (a complementary binding-like sequence) and a 12-mer double-stranded cross-linking adapter sequence (with the cross-linking taking place at two sites) was synthesized (FIG. 3).

As Comparative Example 1, dSS(34) having a sequence complementary to miR21 (a complementary binding-like sequence) and a 12-mer single-stranded adapter sequence was synthesized (FIG. 3).

As Comparative Example 2, d5'DS(12/34) having a sequence complementary to miR21 (a complementary binding-like sequence) and a 12-mer double-stranded adapter sequence was synthesized (FIG. 3).

As Comparative Example 3, d5'HP50 having a sequence complementary to miR21 (a complementary binding-like sequence) and a 12-mer double-stranded adapter sequence, and having a hairpin loop structure comprising four thymidine residues was synthesized (FIG. 3).

As Comparative Example 4, d5'Lig(12/35) having a sequence complementary to miR21 (a complementary binding-like sequence), and a hairpin loop of linear alkyl linker that chemically linked a 12-mer DNA with a 35-mer DNA was synthesized (FIG. 3).

As Comparative Example 5, dSS(46) having a sequence complementary to miR21 (a complementary binding-like sequence) and a 12-mer single-stranded adapter sequence at both ends was synthesized (FIG. 3).

(RNAs Synthesized)

Figure 4:
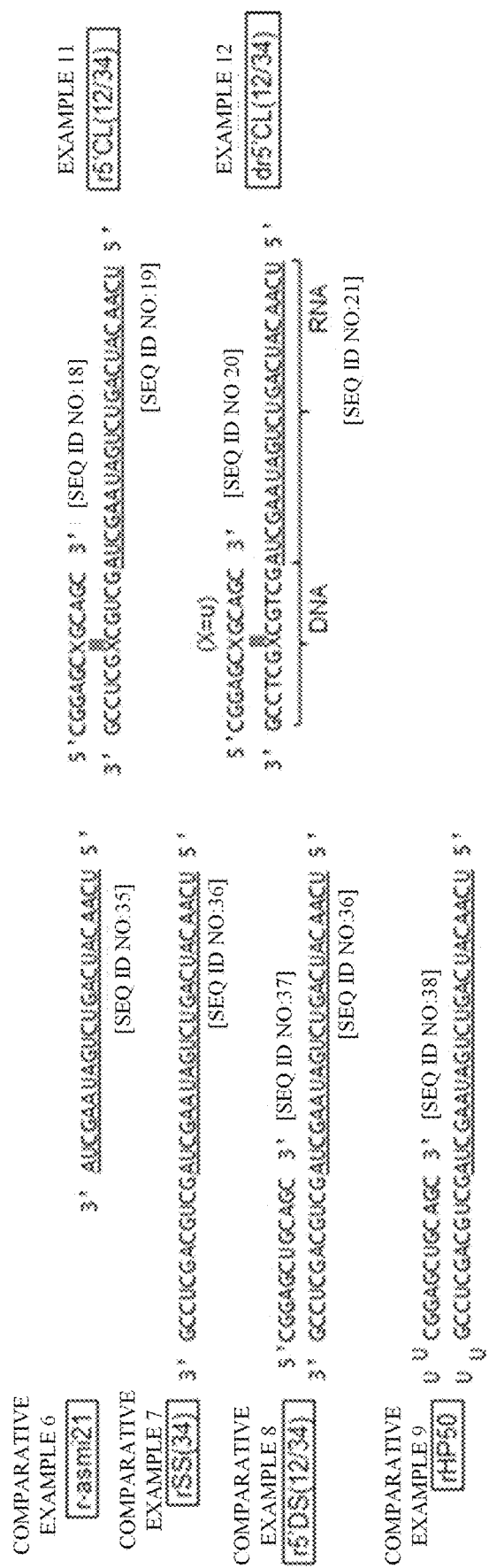
FIG. 4 is a figure showing the base sequences of the nucleic acid complexes (RNAs) of Examples 11 and 12 and the base sequences of the molecules (RNAs) of Comparative Examples 6 to 9.

The sequences of RNAs synthesized are shown in FIG. 4. In FIG. 4, a sequence complementary to miR21 is underlined; "X" in the sequence represents a cross-linking site in the oligonucleotide chain; and the vertical wide line indicates that the nucleic acid strands are together cross-linked by a cross-linking reagent.

As Example 11, r5'CL(12/34) having a sequence complementary to miR21 (a complementary binding-like sequence) and a 12-mer double-stranded cross-linking adapter sequence was synthesized (FIG. 4).

As Example 12, dr5'CL(12/34) (chimeric molecule) having a sequence complementary to miR21 (a complementary binding-like sequence) (RNA) and a 12-mer double-stranded cross-linking adapter sequence (DNA) was synthesized (FIG. 4).

As Comparative Example 6, r-asmi21 comprising a sequence complementary to miR21 (a complementary binding-like sequence) was synthesized (FIG. 4).

As Comparative Example 7, rSS(34) having a sequence complementary to miR21 (a complementary binding-like sequence) and a 12-mer single-stranded adapter sequence was synthesized (FIG. 4).

As Comparative Example 8, r5'DS(12/34) having a sequence complementary to miR21 (a complementary binding-like sequence) and a 12-mer double-stranded adapter sequence was synthesized (FIG. 4).

As Comparative Example 9, rHP50 having a sequence complementary to miR21 (a complementary binding-like sequence) and a 12-mer double-stranded adapter sequence and having a hairpin loop structure comprising four uracil residues was synthesized (FIG. 4).

(2'-OMe RNAs Synthesized)

Figure 5:
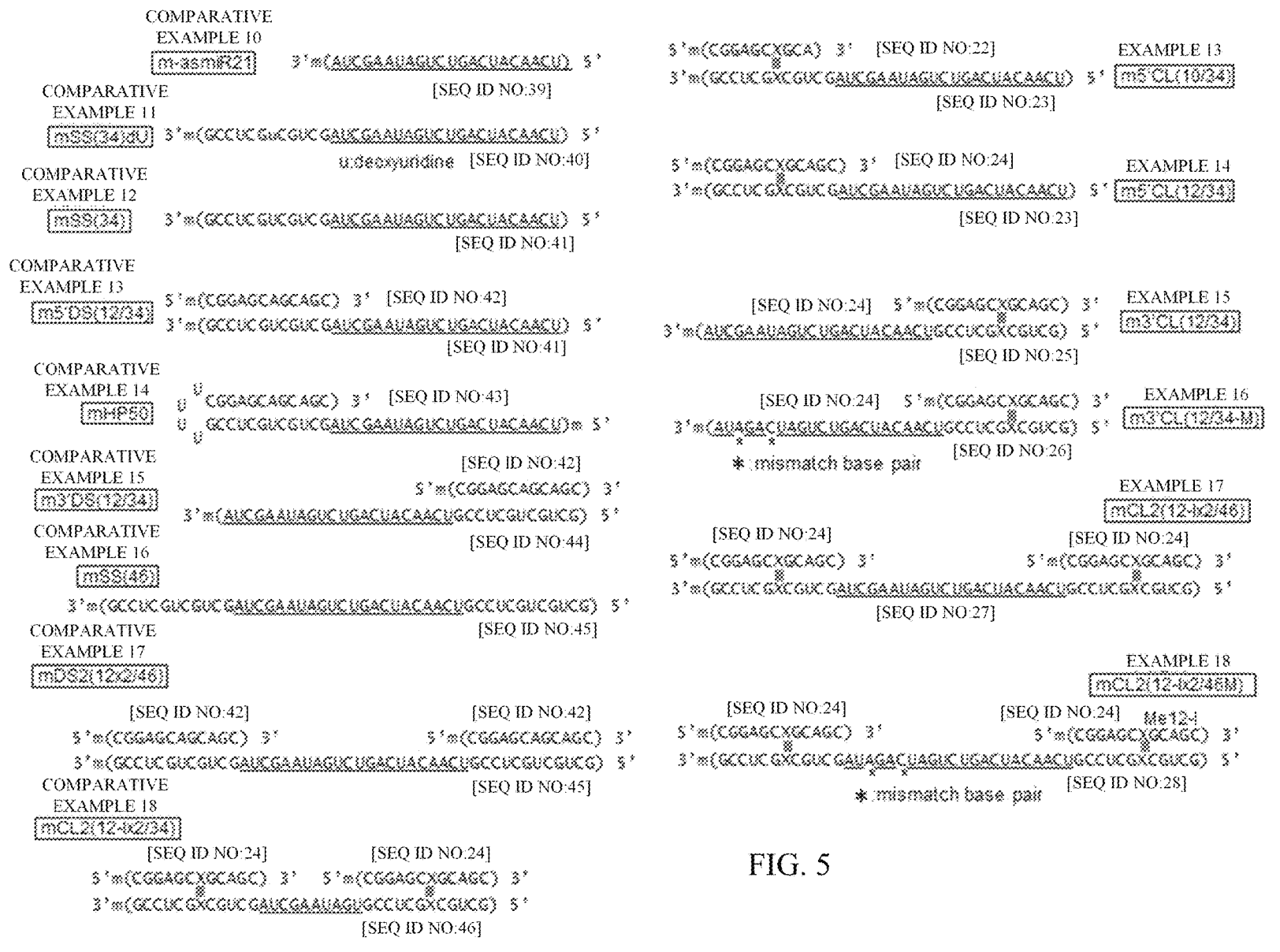

The sequences of 2'-OMe RNAs synthesized are shown in FIG. 5. In FIG. 5, a sequence complementary to miR21 is underlined; "X" in the sequence represents a cross-linking site in the oligonucleotide chain; the vertical wide line indicates that the nucleic acid strands are together cross-linked by a cross-linking reagent; and "m" in the sequence indicates the nucleic acid strand in the parentheses is 2'-OMe RNA.

As Example 13, m5'CL(10/34) having a sequence complementary to miR21 (a complementary binding-like sequence) and a 10-mer double-stranded cross-linking adapter sequence was synthesized (FIG. 5).

As Example 14, m5'CL(12/34) having a sequence complementary to miR21 (a complementary binding-like sequence) and a 12-mer double-stranded cross-linking adapter sequence was synthesized (FIG. 5).

As Example 15, m3'CL(12/34) having a sequence complementary to miR21 (a complementary binding-like sequence) and a 12-mer double-stranded cross-linking adapter sequence at the 3' side was synthesized (FIG. 5).

As Example 16, m3'CL(12/34-M) having a sequence that is not completely complementary to miR21 (with mismatch bases at two sites) (a complementary binding-like sequence) and a 12-mer double-stranded cross-linking adapter sequence at the 3' side was synthesized (FIG. 5).

As Example 17, mCL2(12-1×2/46) having a sequence complementary to miR21 (a complementary binding-like sequence) and a 12-mer double-stranded cross-linking adapter sequence at both ends was synthesized (FIG. 5).

As Example 18, mCL2(12-I×2/46M) having a sequence that is not completely complementary to miR21 (with mismatch bases at two sites) (a complementary binding-like sequence) and a 12-mer double-stranded cross-linking adapter sequence at both ends was synthesized (FIG. 5).

As Comparative Example 10, m-asmiR21 having a sequence complementary to miR21 (a complementary binding-like sequence) was synthesized (FIG. 5).

As Comparative Example 11, mSS(34)dU having a sequence complementary to miR21 (a complementary binding-like sequence) and a 12-mer single-stranded adapter sequence was synthesized (FIG. 5).

As Comparative Example 12, mSS(34) having a sequence complementary to miR21 (a complementary binding-like sequence) and a 12-mer single-stranded adapter sequence was synthesized (FIG. 5).

As Comparative Example 13, m5'DS(12/34) having a sequence complementary to miR21 (a complementary binding-like sequence) and a 12-mer double-stranded adapter sequence was synthesized (FIG. 5).

As Comparative Example 14, mHP50 having a sequence complementary to miR21 (a complementary binding-like sequence) and a 12-mer double-stranded adapter sequence and having a hairpin loop structure comprising four uracil residues was synthesized (FIG. 5).

As Comparative Example 15, m3'DS(12/34) having a sequence complementary to miR21 (a complementary binding-like sequence) and a 12-mer double-stranded adapter sequence at the 3' side was synthesized (FIG. 5).

As Comparative Example 16, mSS(46) having a sequence complementary to miR21 (a complementary binding-like sequence) and a 12-mer single-stranded cross-linking sequence at both ends was synthesized (FIG. 5).

As Comparative Example 17, mDS2(12×2/46) having a sequence complementary to miR21 (a complementary binding-like sequence) and a 12-mer double-stranded cross-linking sequence at both ends was synthesized (FIG. 5).

As Comparative Example 18, mCL2(12-I×2/34) having a sequence with a region hybridizing with miR21 of about 10 bases and a 12-mer double-stranded cross-linking adapter sequence at both ends was synthesized (FIG. 5).

(Synthesis and Purification of Oligonucleotides)

In order to prepare the molecules of Examples 1 to 18 and Comparative Examples 1 to 18, oligonucleotides were each synthesized as shown in Table 1 and Table 2. It is to be noted that, in Table 1 and Table 2, "m" in the sequence indicates that the nucleic acid strand in the parentheses is 2'-OMe RNA and "X" represents "u: deoxyuridine".

TABLE 1

| | | |
|---|---|---|
| Example 1<br>d5' CL(12/34) | 5' CGGAGCXGCAGC 3' | SEQ ID NO: 3 |
| | 3' GCCTCGXCGTCGATCGAATAGTCTGACTACAACT 5' | SEQ ID NO: 4 |
| Example 2<br>d5' CL(12/34T) | 5' CGGAGCXGCAGC 3' | SEQ ID NO: 3 |
| | 3' GCCTCGXCGTCGTATCGAATAGTCTGACTTACAACT 5' | SEQ ID NO: 5 |
| Example 3<br>d5' CL(12/34P) | 5' CGGAGCXGCAGC 3' | SEQ ID NO: 3 |
| | 3' GCCTCGXCGTCGPATCGAATAGTCTGACTACAACT 5' | SEQ ID NO: 6<br>SEQ ID NO: 7 |
| Example 4<br>d5' CL(12/34T8) | 5' CGGAGCXGCAGC 3' | SEQ ID NO: 3 |
| | 3' GCCTCGXCGTCGTTTTTTTTATCGAATAGTCTGACTACAACT 5' | SEQ ID NO:8 |
| Example 5<br>d5' CL(12-5M/34) | 5' CGGTGCXGCAGC 3' | SEQ ID NO: 9 |
| | 3' GCCTCGXCGTCGATCGAATAGTCTGACTACAACT 5' | SEQ ID NO: 4 |
| Example 6<br>d5' CL(12-3M/34) | 5' CGGAGCXGCTGC 3' | SEQ ID NO: 10 |
| | 3' GCCTCGXCGTCGATCGAATAGTCTGACTACAACT 5' | SEQ ID NO: 4 |
| Example 7<br>d5' CL(12/37) | 5' XGGAGCCGCAGC 3' | SEQ ID NO: 11 |
| | 3' TTTXCCTCGGCGTGGATCGAATAGTCTGACTACAACT 5' | SEQ ID NO: 12 |
| Example 8<br>d5' HP CL(50) | 3' CGACGXGCGAGGCTTTTGCCTCGXCGTCGATCGAATAGTCTGACTACAACT 5' | SEQ ID NO: 13 |
| Example 9<br>dCL2(12-I, II/46 | 5' CGGAGCXGCAGC 3' | SEQ ID NO: 3 |
| | 5' GTGCGXGATCGA 3' | SEQ ID NO: 14 |
| | 3' GCCTCGXCGTCGATCGAATAGTCTGACTACAACTCACGCXCTAGCT 5' | SEQ ID NO: 15 |
| Example 10<br>dCL2(12/34) | 5' CCXAGCGGCXGC 3' | SEQ ID NO: 16 |
| | 3' GCXTCGCCGXCGATCGAATAGTCTGACTACAACT 5' | SEQ ID NO. 17 |
| Example 11<br>r5' CL(12/34) | 5' CCGACCAGCAGC 3' | SEQ ID NO: 18 |
| | 3' GCCUCGXCGUCGAUCGAAUAGUCUGACUACAACU 5' | SEQ ID NO: 19 |
| Example 12<br>dr5' CL(12/34) | 5' CGGAGCXGCAGC 3' | SEQ ID NO: 20 |
| | 3' GCCTCGXCGTGGAUCGAAUAGUCUGACUACAACU 5' | SEQ ID NO: 21 |
| Example 13<br>m5' CL(10/34) | 5' m(CGGAGCXGCA) 3' | SEQ ID NO: 22 |
| | 3' m(GCCUCGXCGUCGAUCGAAUAGUCUGACUACAACU) 5' | SEQ ID NO: 23 |
| Example 14<br>m5' CL(12/34) | 5' m(CGGAGCXGCAGC) 3' | SEQ ID NO: 24 |
| | 3' m(GCCUCGXCGUCGAUCGAAUAUCUGACUACAACU) 5' | SEQ ID NO: 23 |
| Example 15<br>m5' CL(12/34) | 5' m(CGGAGCXGCAGC) 3' | SEQ ID NO: 24 |
| | 3' m(AUCGAAUAGUCUGACUACAACUGCCUCGXCGUCG) 5' | SEQ ID NO: 25 |

TABLE 1-continued

| | | |
|---|---|---|
| Example 16 m3' CL(12/34-M) | 5' m(CGGAGCXGCAGC) 3' | SEQ ID NO: 24 |
| | 3'm(AUAGACUAGUCUGACUAACAACUGCCUCGXCGUCG) 5' | SEQ ID NO: 26 |
| Example 17 mCL2(12-1x2/46) | 5' m(CGGAGCXGCAGC) 3' | SEQ ID NO: 24 |
| | 5' m(CGGAGCXGCAGC) 3' | SEQ ID NO: 24 |
| | 3' m(GCCUCGXCGUCGAUCGAAUAGUCUGACUACAACUGCCUCGXCGUCG) 5' | SEQ ID NO: 27 |
| Example 18 mCL2(12-1x2/46M) | 5' m(CGGAGCXGCAGC) 3' | SEQ ID NO: 24 |
| | 5' m(CGGAGCXGCAGC) 3' | SEQ ID NO: 24 |
| | 3' m(GCCUCGXCGUCGAUAGACUAGUCUGACUACAACUGCCUCGXCGUCG) 5' | SEQ ID NO: 28 |

TABLE 2

| | | |
|---|---|---|
| Comparative Example 1 dSS(34) | 3' GCCTCGuCGTCGATCGAATAGTCTGACTACAACT 5' (udeoxyuridine) | SEQ ID NO: 29 |
| Comparative Example 2 d5' DS(12/34) | 5' CGGAGCACCACC 3' | SEQ ID NO: 30 |
| | 3' GCCTCGuCGTCGATCGNVAGTCTGACTACAACT 5' (udeoxyuridine) | SEQ ID NO: 29 |
| Comparative Example 3 d5' HP50 | 3' CGACGTCGAGGCTTTTGCCTCGACGTGGATCGAATAGTCTGACTACAACT 5' | SEQ ID NO: 31 |
| Comparative Example 4 d5' Lig(12/35) | 5' CGGAGCACTCAGC 3' | SEQ ID NO: 32 |
| | 3' UGCCTCGuCGTCGATCGAATAGTCTGACTACAACT 5' | SEQ ID NO: 33 |
| Comparative Example 5 dSS(46) | 3' GCCTCGuCGTCGATCGAATAGTCTGACTACAACTCACGCuCTAGCT 5' (urdeoxyuridine) | SEQ ID NO: 34 |
| Comparative Example 6 r-asmi21 | 3' AUCGAAUAGUCUGACUACAACU 5' | SEQ ID NO: 35 |
| Comparative Example 7 rSS(34) | 3' GCCUCGACGUCGAUCGAAUAGUCUGACUACAACU 5' | SEQ ID NO: 36 |
| Comparative Example 8 r5' DS(12/34) | 5' CGGAGCUGCAGC 3' | SEQ ID NO: 37 |
| | 3' GCCUCGACGUCGAUCGAAUAGUCUGACUACAACU 5' | SEQ ID NO: 36 |
| Comparative Example 9 rHP50 | 3' CGACGUCGAGGCUUUUGCCUCGACGUCGAUCGAAUAGUCUGACUACAACU 5' | SEQ ID NO: 38 |
| Comparative Example 10 m-asmiR21 | 3' m(AUCGAAUAGUCUGACUACAACU) 5' | SEQ ID NO: 39 |
| Comparative Example 11 mSS(34)dU | 3' m(GCCUCGuCGUCGAUCGAAUAGUCUGACUACAACU)5' (udeoxyuridine) | SEQ ID NO: 40 |
| Comparative Example 12 mSS(34) | 3' m(GCCUCGUCGUCGAUGCAAUAGUCUGACUACAAU) 5' | SEQ ID NO: 41 |
| Comparative Example 13 m5'DS(12/34) | 5' m(CGGAGCAGCAGC)3' | SEQ ID NO: 42 |
| | 3' m(GCCUCGuCGUCGAUCGAAUAGUCUGACUACAACU)5' | SEQ ID NO: 41 |

TABLE 2-continued

| | | |
|---|---|---|
| Comparative Example 14 mHP50 | 3 m(CGACGACGAGGCUUUUGCCUCGUCGUCGAUCGAAUAGUCUGACUACAACU)m5' | SEQ ID NO: 43 |
| Comparative Example 15 m3'DS(12/34) | 5' m(CGGAGCAGCAGC) 3'<br>3' m(AUCGAAUAGUCUGACUACAACUGCCUCGUCGUCG)5' | SEQ ID NO: 42<br>SEQ ID NO: 44 |
| Comparative Example 16 mSS(46) | 3' m(GCCUCGUCGUCGAUCGAAUAGUCUGACUACAACUGCCUCGUCGUCG) 5' | SEQ ID NO: 45 |
| Comparative Example 17 mDS2(12x2/46) | 5' m(CGGAGCAGCAGC) 3'<br>5' m(CGGAGCAGCAGC) 3'<br>3' m(GCCUCGXCGUCGACGAAUAGUGCCUCGXCGUCG) 5' | SEQ ID NO: 42<br>SEQ ID NO: 42<br>SEQ ID NO: 45 |
| Comparative Example 18 mCL2(12-b(2/34) | 5' m(CGGAGCXGCAGC) 3'<br>5' m(CGGAGCXGCAGC) 3'<br>3' m(GCCUCGXCGUCGAUCGAAUAGUGCCUCGXCGUCG) 5' | SEQ ID NO: 24<br>SEQ ID NO: 24<br>SEQ ID NO: 46 |

The synthesis of the oligonucleotide was carried out using 3'-phosphoramidite (Glen Research) on an automated DNA·RNA synthesizer (model 3900; manufactured by PerkinElmer Japan Co., Ltd., Applied Biosystems division). The oligonucleotide was synthesized at 0.2 μmol scale. HPLC was carried out using Gilson's device and analysis was carried out using Waters 996 photodiode array detector.

After the synthesis was completed, a CPG (Controlled Pore Glass) to which the synthesized oligonucleotide was bound was heated in an ammonia-methylamine mixture (28% conc. ammonium water: 40% methylamine in water=1:1.2 mL) at 65° C. for 10 minutes to 15 minutes to cleave the oligonucleotide from the CPG and to carry out deprotection in the base moiety and the phosphodiester moiety. A reaction solution was collected and the solvent was evaporated to be removed.

DNA and 2'-O-methyl RNA (2'-OMe RNA) were dissolved in 2 mL of 0.2 M triethylamine acetate (pH 7.0) and subjected to a reversed phase open column (YMC cartridge 500 mg) to be thereby partially purified.

As for RNA, the solvent was evaporated to be removed after the deprotection reaction. The residues were added with dimethyl sulfoxide (115 μL), triethylamine (60 μL), and triethylamine trihydrofluoride (75 μL) and stirred to be dissolved, followed by heating at 65° C. for 2.5 hours. To the reaction solution, 1.75 mL of 1.8 M triethylamine acetate (pH 7.0); and the resultant was subjected to a reversed phase open column for partial purification.

The purified oligonucleotides (DNA, RNA, and 2'-OMe RNA) were purified by high performance liquid chromatography (HPLC). HPLC is carried out using Gilson's device connected to Waters μ-Bondasphere C18 300A (inner diameter: 3.9 mm×length 150 mm, Waters Corporation). In the case of a reversed phase, a concentration gradient of acetonitrile in 0.1 M triethylamine acetate buffer (TEAA, pH 7.0) was employed as a mobile phase. The types of the oligonucleotides synthesized and conditions for reversed phase HPLC are shown below.
Solution A: 5% acetonitrile/0.1 M TEAA (pH 7.0)
Solution B: 25% acetonitrile/0.1 M TEAA (pH 7.0)

Preparation of DNA Products with One Cross-Link (CL1) and DNA Products with Two Cross-Links (CL2) (Examples 1 to 10)

A product with one cross-link of d5'CL(12/34) (Example 1, FIG. 3) was prepared by the following method. The nucleic acid strand of SEQ ID NO: 3 (3.0 nmol) and the nucleic acid strand of SEQ ID NO: 4 (2.52 nmol), both of which contained deoxyuridine (hereinafter dU), were dissolved in a solution (the total amount of 198.5 μL) containing a Uracil DNA glycosylase (UDG) buffer (×10, NEW ENGLAND Labs., 20 μL). The reaction solution was heated at 90° C. for a minute, cooled with ice, and allowed gradually to cool to room temperature; and left to stand for five minutes in the stages at room temperature and 0° C. Subsequently, UDG (NEW ENGLAND Labs., 7.5 units, 1.5 L) was added to the reaction solution; and the mixture was reacted in the total amount of 200 μL at 37° C. for 60 minutes and then left to stand at 4° C. for 15 minutes. To this reaction solution, 2 mM aoNao (25.2 nmol, 12.6 μL) was added; and the mixture was reacted at 17° C. for three hours. Purification was thereafter carried out by using HPLC with a reversed phase column to obtain a product with a cross-link or cross-links. The following solutions were used for the purification.
Solution A: 5% acetonitrile/0.1 M TEAA (pH 7.0)
Solution B: 25% acetonitrile/0.1 M TEAA (pH 7.0)

A style of s bond between sugars of the nucleic acid strand of SEQ ID NO: 3 and the nucleic acid strand of SEQ ID NO: 4 in d5'CL(12/34) (Example 1) will be described (FIG. 6A). When the nucleic acid strands of SEQ ID NO: 3 and SEQ ID NO: 4 are treated with UDG, an AP site is formed in the deoxyuridine in the nucleic acid strand (FIG. 6A (i)). AP sites exist in an equilibrium state; and an open ring form thereof has an aldehyde group. When added thereto, the cross-linking reagent (aoNao) binds and reacts with the aldehyde group described above; and the nucleic acid strand of SEQ ID NO: 3 and the nucleic acid strand of SEQ ID NO: 4 are thereby cross-linked (FIG. 6A (ii)). In FIG. 6A, the reactions of (i) and (ii) can proceed in stages or at the same time. It is to be noted that the style of the bond between the sugars of the two nucleic acid strands of the double-stranded cross-linking adapter sequence in Examples 2 to 18 and Comparative Example 18 is the same as that of the above Example 1.

Other products with one cross-link were prepared in the same manner as described above using the nucleic acid strand of SEQ ID NO: 3 and the nucleic acid strand of SEQ ID NO: 5 for d5'CL(12/34T) (Example 2), using the nucleic acid strand of SEQ ID NO: 3 and a sequence with SEQ ID NO: 6 and SEQ ID NO: 7 being linked via a propyl linker (Table 1) for d5'CL(12/34P) (Example 3), using the nucleic acid strand of SEQ ID NO: 3 and the nucleic acid strand of SEQ ID NO: 8 for d5'CL(12/34T8) (Example 4), using the nucleic acid strand of SEQ ID NO: 9 and the nucleic acid strand of SEQ ID NO: 4 for d5'CL(12-5M/34) (Example 5), and using the nucleic acid strand of SEQ ID NO: 10 and the nucleic acid strand of SEQ ID NO: 4 for d5'CL(12-3M/34) (Example 6).

d5'CL(12/37) (Example 7) having a cross-linking moiety at the end was prepared by a cross-linking reaction of 12-mer (d12Z-I) (SEQ ID NO: 11) in which an amidite reagent for 12-mer abasic site (abasic II phosphoramidite, Glen research) is bound at the 5' end with d37dU (SEQ ID NO: 12) having a sequence complementary thereto (because UDG did not work on the end of oligonucleotide, a reagent capable of generating the AP site was, for the preparation, introduced at the stage of oligonucleotide synthesis and cross-linked). For the purpose of presenting the abasic site to the 5' end, d12Z-I (4 nmol) was in advance subjected to acid treatment (left to stand in 50 μL of 80% acetic acid at room temperature for 30 minutes) and added with 2 M TEAA (200 μL) for neutralization, followed by desalting on NAP-5. This resultant was added to d37dU (2 nmol) that had been treated with UDG in the same method as described for the above d5'CL(12/34) (Example 1) and placed on ice for five minutes; and 2 mM aoNao (20 nmol, 10 μL) was added thereto to react at 17° C. for 16 hours. Purification was then carried out using HPLC with a reversed phase column, thereby obtaining a product with a cross-link or cross-links.

As for d5'HP CL(50) (Example 8) which was a 50-mer single-stranded product with a cross-link having a hairpin loop, the same reaction as described for the above d5'CL(12/34) (Example 1) was carried out using a 50-mer oligonucleotide (dHP50dUdU, SEQ ID NO: 13) with deoxyuridines in a facing portion of double strands, followed by the purification using reversed phase HPLC.

As for dCL2(12-I,II/46) (Example 9) which is a product with two cross-links, the nucleic acid strand of SEQ ID NO: 3 (7.56 nmol) and the nucleic acid strand of SEQ ID NO: 14 (7.56 nmol) was mixed with the nucleic acid strand of SEQ ID NO: 15 (2.52 nmol) and the mixture was subjected to a UDG reaction in the same method as described for d5'CL (12/34) (Example 1). Thereafter, 2 mM aoNao (50.4 nmol, 25.2 μL) was added thereto and the mixture was subjected to a cross-linking reaction and purification in the same manner as described for d5'CL(12/34) (Example 1).

As for dCL2(12/34) (Example 10) which is a product with two cross-links, d12dUdU (SEQ ID NO: 16) (2.4 nmol) and d34dUdU (SEQ ID NO: 17) (2.0 nmol) were mixed and the mixture was subjected to a UDG reaction in the same method as described for d5'CL(12/34) (Example 1). Thereafter, 2 mM aoNao (40 nmol, 20 μL) was added thereto and the mixture was subjected to a cross-linking reaction and purification in the same manner as described for d5'CL(12/34) (Example 1).

Preparation of DNA Products with No Cross-Links (DS) (Comparative Examples 2 to 4)

d5'DS(12/34) (Comparative Example 2) was prepared by adding the nucleic acid strand of SEQ ID NO: 30 and the nucleic acid strand of SEQ ID NO: 29 at equimolar amounts and carrying out purification in the same manner as described for d5'CL(12/34) (Example 1).

d5'HP50 (Comparative Example 3) having a hairpin loop was prepared by carrying out a reaction using the nucleic acid strand of SEQ ID NO: 31 in the same method as described for the above d5'CL(12/34) (Example 1).

d5'Lig(12/35) (Comparative Example 4) which was a hairpin loop oligonucleotide having an alkyl linker was prepared from the following a ligation reaction. As for this reaction, employed was a reaction in which the ligation was achieved by allowing an oligonucleotide having a primary amino group to work on an oligonucleotide with an aldehyde group being generated at 3' end to reduce a Schiff base. At the time of the preparation, Kojima, N., Sugino, M., Mikami, A. Nonaka, K., Fujinawa, Y.; Muto, I., Matsubara, K., Ohtsuka, E. and Komatsu, Y. Enhanced reactivity of amino-modified oligonucleotides by insertion of aromatic residue. Bioorg. Med. Chem. Lett., 2006, 16, 5118-5121 was used as a reference.

First, d35dU-rU (SEQ ID NO: 33) (2 nmol) in a 100 mM phosphate buffer (pH 6) was acted on by periodate (16 nmol) (reaction solution 48 μL) and heated at 27° C. for 90 minutes, thereby oxidizing the 3' end. Subsequently, aminated oligonucleotide (ssH-d12A; 2.4 nmol) (SEQ ID NO: 32) which had a sequence complementary to d35dU-rU and had an amino linker (ssH-linker; Sigma Ald.) at the 5' end was dissolved in sterilized water (6 μL) and added to d35dU-rU that had been in advance oxidized. The mixed solution was left to stand on ice for five minutes and then a binding reaction was carried out in the presence of 150 mM sodium cyanoborohydride (reaction solution 60 μL) at 27° C. for 16 hours. After the reaction, like the cross-linked oligonucleotide, the linked product was purified by reversed phase HPLC. A synthesis scheme for d5'Lig(12/35): SEQ ID NO: 32 and SEQ ID NO: 33 (Comparative Example 4) is shown below.

With regard to the purified cross-linking adapter (Example 1 and Example 9), the molecular weight was checked by LC-MS and, at the same time, whether the cross-linking was achieved was checked by carrying out 20% denaturing polyacrylamide gel electrophoresis. To be more specific, it was confirmed, as shown in FIG. 7A, that the product with one cross-link of Example 1 migrated more slowly than the nucleic acid strand of SEQ ID NO: 3 and the nucleic acid strand of SEQ ID NO: 4 which were raw materials and the product with two cross-links of Example 9 migrated more slowly than the nucleic acid strand of SEQ ID NO: 15 which was a raw material. As for gel analysis, the gel was stained with SYBR (registered trademark) Gold (Life Technologies) after the electrophoresis and analyzed by Typhoon FLA9000 (GE Healthcare).

HPLC conditions used in the purification of each molecule and the results of molecular weight measurement for each molecule are shown in Table 3.

TABLE 3

| | | HPLC condition (B %/20 min, temperature) | ESI-MS |
|---|---|---|---|
| Example 1 | d5'CL(12/34) | 20-35%, rt | calc. 14097.44, found 14100.21 |
| Example 2 | d5'CL(12/34T) | 25-40%, rt | calc. 14401.4872, found 14404.13 |

TABLE 3-continued

| | | HPLC condition (B %/20 min, temperature) | ESI-MS |
|---|---|---|---|
| Example 3 | d5'CL(12/34P) | 25-40%, rt | calc. 14235.4492, found 14238.96 |
| Example 4 | d5'CL(12/34T8) | 25-40%, rt | calc. 16530.8122, found 16533.6 |
| Example 5 | d5'CL(12-5M/34) | 0-40%, 50° C. | calc. 14088.4292, found 14090.94 |
| Example 6 | d5'CL(12-3M/34) | 0-40%, 50° C. | calc. 14088.4292, found 14091.01 |
| Example 7 | d5'HP CL(12/37) | 0-100%, 50° C. | calc. 15009.5792, found 15012.79 |
| Example 8 | d5'HP CL(50) | 20-40%, 60° C. | calc. 15377.5852, found 15378.75 |
| Example 9 | dCL2(12-I, II/46) | 25-40%, rt | calc. 21495.7254, found 21495.8 |
| Example 10 | dCL2(12/34) | 25-40%, rt | calc. 14141.4614, found 14143.84 |
| Comparative Example 4 | d5'HP Lig(12/35) | 10-50%, 50° C. | calc. 14579.53, found 14581.59 |

Figure 6B:
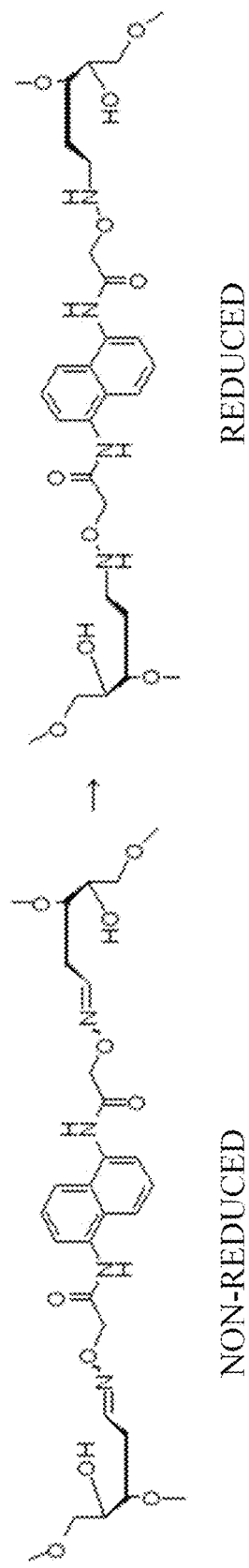
FIG. 6B is a figure illustrating a reduction reaction by sodium cyanoborohydride ($NaBH_3CN$)

Preparation of RNA Products with One Cross-Link (CL1) (Examples 11 and 12)

r5'CL(12/34) (Example 11, FIG. 4) which was a product with one cross-link was prepared by the following method. The nucleic acid strand of SEQ ID NO: 18 (7.56 nmol) and the nucleic acid strand of SEQ ID NO: 19 (2.52 nmol) were dissolved in a solution containing a UDG buffer (×10, 20 μL) (the total amount 198.5 μL). The reaction solution was heated at 90° C. for a minute, cooled with ice, and allowed gradually to cool to room temperature; and left to stand for five minutes in the stages at room temperature and 0° C. Subsequently, UDG (7.5 unit, 1.5 μL) was added to the reaction solution. The mixture of the total amount 200 μL was then subjected to reaction at 37° C. for 60 minutes and thereafter left to stand at 4° C. for 15 minutes. To this reaction solution, 2 mM aoNao (25.2 nmol, 12.6 μL) was added; and the mixture was heated at 27° C. to carry out a cross-linking reaction. After two hours, the reaction solution was subjected to a reduction reaction in a composition of 100 mM phosphate buffer solution (pH 1.07) and 200 mM sodium cyanoborohydride (NaBH$_3$CN) (FIG. 6B). After 30-minute reaction at room temperature, 2 M TEAA buffer (420 μL) was added for neutralization; and a product with a cross-link was purified using HPLC with a reversed phase column. As for the HPLC solution, the purification was carried out using the same solution as used for DNA. dr5'CL(12/34) (Example 12) which was also a product with one cross-link was prepared using the nucleic acid strand of SEQ ID NO: 20 and the nucleic acid strand of SEQ ID NO: 21 in the same manner as described above.

HPLC conditions used in the purification of each of the products with a cross-link are shown in Table 4.

TABLE 4

| | | HPLC condition (B %/20 min, temperature) |
|---|---|---|
| Example 11 | r5'CL(12/34) | 15-35%, rt |
| Example 12 | dr5'CL(12/34) | 20-40%, rt |

Preparation of RNA Products with No Cross-Links (DS) (Comparative Examples 8 and 9)

r5'DS(12/34) (Comparative Example 8) was prepared by adding the nucleic acid strand of SEQ ID NO: 37 and the nucleic acid strand of SEQ ID NO: 36 at equimolar amounts and carrying out purification in the same manner as described for r5'CL(12/34) (Example 11).

rHP50 (Comparative Example 9) having a hairpin loop was prepared by carrying out a reaction using the nucleic acid strand of SEQ ID NO: 38 in the same method as described for the above r5'CL(12/34) (Example 11).

Preparation of 2'-OMe RNA Products with One Cross-Link (CL1) and RNA Products with Two Cross-Links (CL2) (Examples 13 to 18)

m5'CL(12/34) (Example 14, FIG. 5) which was a product with one cross-link in the 5' side was prepared by the following method. The nucleic acid strand of SEQ ID NO: 24 (3.0 nmol) and the nucleic acid strand of SEQ ID NO: 23 (2.52 nmol), both of which contained dU, were dissolved in a solution containing a UDG buffer (×10, 20 μL) (the total amount 198.5 μL). The reaction solution was heated at 90° C. for a minute, cooled with ice, and allowed gradually to cool to room temperature; and left to stand for five minutes in the stages at room temperature and 0° C. Subsequently, UDG (7.5 unit, 1.5 μL) was added to the reaction solution. The mixture of the total amount 200 μL was then subjected to reaction at 37° C. for 60 minutes and thereafter left to stand at 4° C. for 15 minutes. To this reaction solution, 2 mM aoNao (25.2 nmol, 12.6 μL) was added to carry out a reaction at 27° C. for three hours. Thereafter, purification was carried out using HPLC with a reversed phase column to obtain a product with a cross-link or cross-links. With regard to other products with one cross-link, the same method as described above was carried out from the reaction to the purification using: the nucleic acid strand of SEQ ID NO: 23 and the nucleic acid strand of SEQ ID NO: 22 for m5'CL(10/34) (Example 13, FIG. 5); the nucleic acid strand of SEQ ID NO: 25 and the nucleic acid strand of SEQ ID NO: 24 for m3'CL(12/34) (Example 15, FIG. 5); and the nucleic acid strand of SEQ ID NO: 26 and the nucleic acid strand of SEQ ID NO: 24 for m3'CL(12/34-M) (Example 16, FIG. 5). As for the HPLC solution, the purification was carried out using the same solution as described above (preparation of DNAs).

With regard to mCL(12-I×2/46) (Example 17, FIG. 5) which was a product with two cross-links, the nucleic acid strand of SEQ ID NO: 24 (7.56 nmol) and the nucleic acid strand of SEQ ID NO: 27 (2.52 nmol) were mixed and subjected to a UDG reaction by the same method as described for the product with one cross-link of m5'CL(12/34) (Example 14). Thereafter, 2 mM aoNao (50.4 nmol, 25.2 μl) was added thereto and the mixture was subjected to a cross-linking reaction and purification in the same manner as described for m5'CL(12/34) (Example 14). mCL(12-I×2/46M) (Example 18) which was also a product with two cross-links, the same method as described above was carried out from the reaction to the purification using the nucleic acid strand of SEQ ID NO: 24 and the nucleic acid strand of SEQ ID NO: 28 in the same manner as described above.

Preparation of 2'-OMe RNA Molecules (Comparative Examples 13 to 15, 17, and 18)

m5'DS(12/34) (Comparative Example 13) was prepared by adding the nucleic acid strand of SEQ ID NO: 42 and the nucleic acid strand of SEQ ID NO: 41 at equimolar amounts and carrying out purification in the same manner as described for m5'CL(12/34) (Example 14); m3' DS(12/34) (Comparative Example 15) was prepared by adding the nucleic acid strand of SEQ ID NO: 42 and the nucleic acid strand of SEQ ID NO: 44 at equimolar amounts and carrying out the purification; and mDS2(12×2/46) (Comparative Example 17) was prepared by adding the nucleic acid strand of SEQ ID NO: 42 and the nucleic acid strand of SEQ ID NO: 45 at equimolar amounts and carrying out the purification.

mHP50 (Comparative Example 14) having a hairpin loop was prepared by carrying out a reaction using the nucleic acid strand of SEQ ID NO: 43 in the same method as described for the above m5'CL(12/34)(Example 14).

mCL2(12-I×2/34)(Comparative Example 18) having the cross-linking adapter sequence at both ends was prepared using the nucleic acid strand of SEQ ID NO: 24 and the nucleic acid strand of SEQ ID NO: 46 in the same manner as described for m5'CL(12/34) (Example 14).

With regard to the purified molecule with the cross-linking adapter, the molecular weight was checked by LC-MS and, at the same time, whether the cross-linking was achieved was checked by carrying out 20% denaturing polyacrylamide gel electrophoresis. To be more specific, it was confirmed, as shown in FIG. 7B, that the products with one cross-link of Examples 14 to 16 migrated more slowly than the nucleic acid strand of SEQ ID NO: 24 and the nucleic acid strand of mSS(34)dU (Comparative Example 11) which were raw materials and the product with two cross-links of Example 17 and the molecule of Comparative Example 18 migrated more slowly than the nucleic acid strand of SEQ ID NO: 27. As for gel analysis, the gel was stained with SYBR (registered trademark) Gold (Life Technologies) after the electrophoresis and analyzed by Typhoon FLA9000 (GE Healthcare).

HPLC conditions used in the purification of each of the products with a cross-link or cross-links and the results of molecular weight measurement for each of the products with a cross-link or cross-links are shown in Table 5.

TABLE 5

| | | HPLC condition (B %/20 min, temperature) | ESI-MS |
|---|---|---|---|
| Example 13 | m5'CL(10/34) | 0-100%, 50° C. | calc. found |
| Example 14 | m5'CL(12/34) | 0-100%, 50° C. | calc. 15306.78, found 15308.78 |
| Example 15 | m3'CL(12/34) | 0-100%, 50° C. | calc. 15306.78, found 15309.10 |
| Example 16 | m3'CL(12/34-M) | 0-100%, 50° C. | calc. 15306.7842, found 15309.1 |
| Example 17 | mCL2(12-Ix2/46) | 0-100%, 50° C. | calc. 23336.26, found 23339.76 |
| Example 18 | mCL2(12-Ix2/46M) | 0-100%, 50° C. | calc. 23336.2564, found 23339.69 |
| Comparative Example 18 | mCL2(12-Ix2/34) | 0-100%, 50° C. | calc. 19366.56, found 19370.57 |

Example B (Tm Measurement)

With regard to the molecules of the Examples and Comparative Examples which had been prepared in Example A, a melting curve was measured. As nucleic acids to be targeted, miR21 (SEQ ID NO: 1) and miR21-M (SEQ ID NO: 2) were selected.

Figure 8:
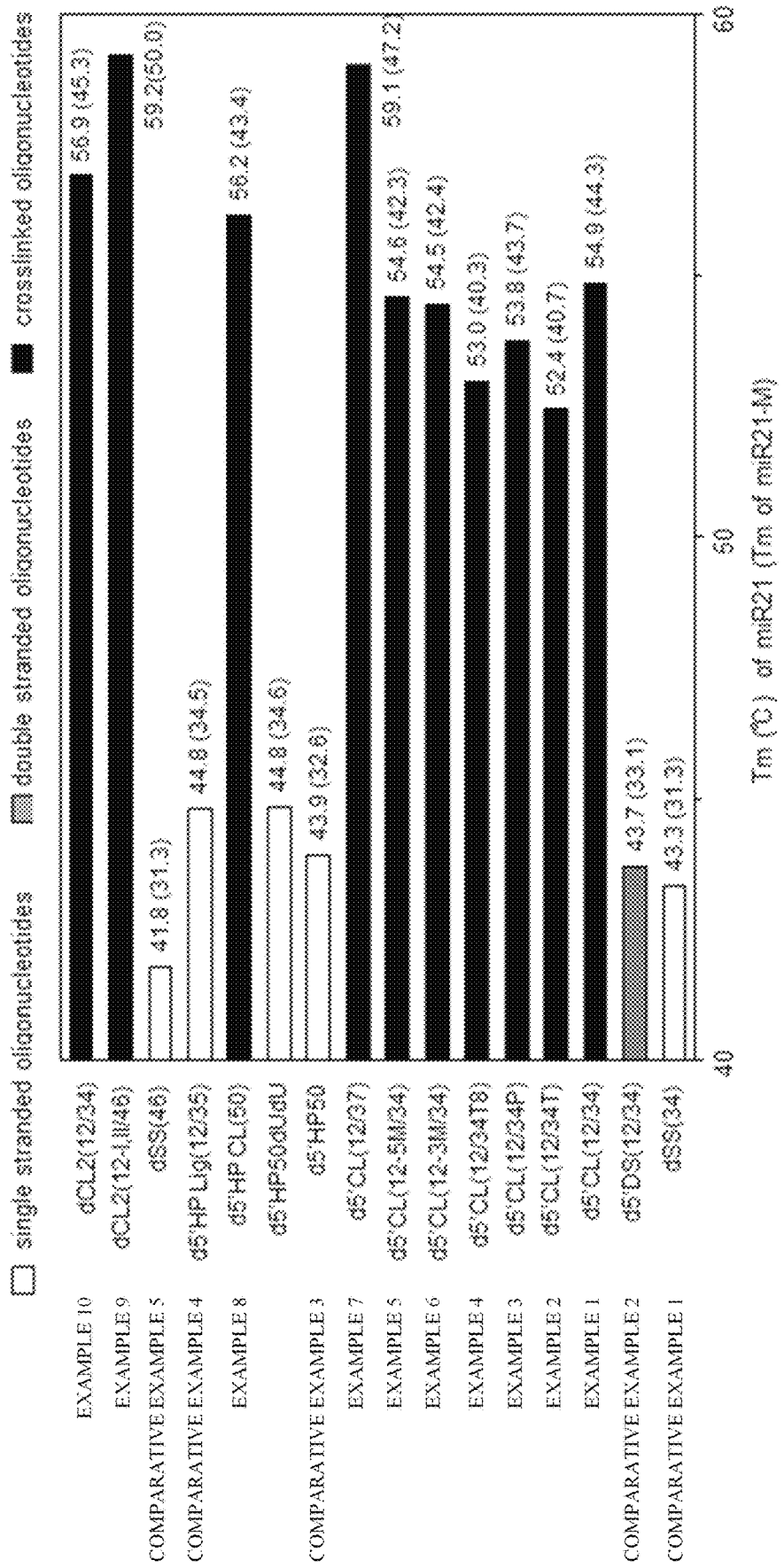
FIG. 8 is a figure of showing the results of Tm value measurement for the nucleic acid complexes of Examples 1 to 10.
Figure 9:
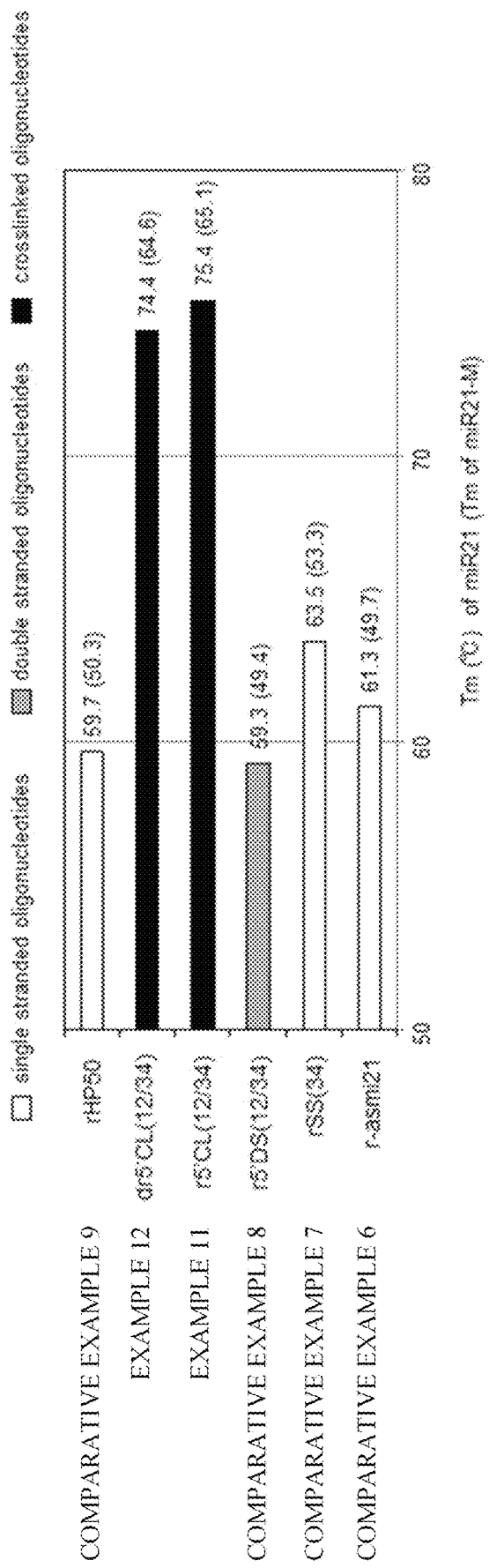
FIG. 9 is a figure of showing the results of Tm value measurement for the nucleic acid complexes of Examples 11 and 12.
Figure 10:
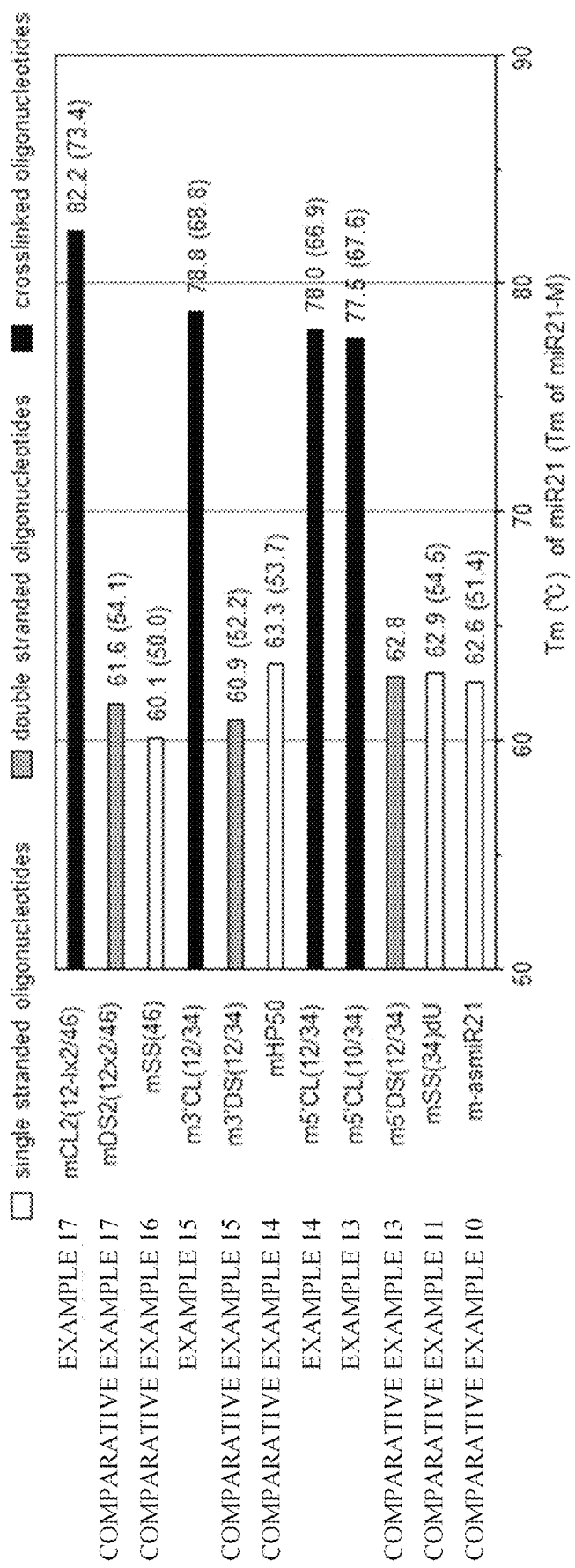
FIG. 10 is a figure of showing the results of Tm value measurement for the nucleic acid complexes of Examples 13 to 15, and 17.

The molecules (130 pmol) of Examples 1 to 15, and 17 or Comparative Examples 1 to 11 and 13 to 17 were mixed with miR-21 or miR-21-M (130 pmol) and the mixture was dissolved in a Tm measurement buffer (10 mM NaCl, 10 mM Na cacodylate (pH 7.0), 130 μL). The sample was heated at 90° C. for three minutes, then allowed to gradually cool to room temperature to anneal, and then left to stand at room temperature for five minutes; and 125 μL of the resultant was placed in a measurement cuvette to measure the melting curve. The measurement was carried out using UV2500PC (manufactured by Shimadzu Corporation) in a temperature range of 5° C. to 90° C. in conditions of a temperature rate of 0.5° C./min, a measurement interval of 0.2° C., start hold 600 seconds, and standby prior to measurement 0 seconds. FIG. 8, FIG. 9, and FIG. 10 show the results of the Tm measurement for Examples 1 to 10 and Comparative Examples 1 to 5 (DNA), the results of the Tm measurement for Examples 11 and 12 and Comparative Examples 6 to 9 (RNA), and the results of the Tm measurement for Examples 13 to 15 and 17 and Comparative Examples 10, 11, and 13 to 17 (2'-OMe RNA), respectively. It is to be noted that, in FIGS. 8 to 10, numerical values in the parentheses shown in the left of the bar chart indicate Tm values for miR21-M (SEQ ID NO: 2).

As shown in FIG. 8, Comparative Example 2 which had the double-stranded adapter sequence showed a Tm value comparable to Comparative Examples 1 and 5 which had the single-stranded adapter sequence. In addition, d5'HP50 (Comparative Example 3) and d5'Lig(12/35) (Comparative Example 4, both of which had the hairpin loop comprising nucleotides or an alkyl linker also showed a Tm value comparable to Comparative Examples 1 and 5 which had the single-stranded adapter sequence. On the other hand, Examples 1 to 8 which had the cross-linking adapter sequence exhibited a higher Tm value by 10° C. or more, as compared with that of Comparative Examples 1 to 5; and Example 9 which was the product with two cross-links (CL2) exhibited a much higher Tm value. While the cross-linking of the double stranded part was observed to also increase the Tm value of the oligonucleotide having the hairpin loop (d5'HP CL(50): Example 8) to 56° C., the oligonucleotide before the cross-linking (d5'HP50dUdU, SEQ ID NO: 13) had a lower Tm value and did not produce the stabilization effect, demonstrating therefore that the cross-linking required for the increase in the Tm value. In addition, in the case in which the cross-linking site was located at the end of the adapter (d5'CL(12/37): Example 7), a higher Tm value was observed. It is to be noted that the products with one cross-link (CL1) of Examples 5 and 6 which have a mismatch in the cross-linking adapter sequence also exhibited a Tm value comparable to Examples 1 which was also the product with one cross-link (CL1). Further, it was also confirmed that Example 2 which was the product with one cross-link (CL1) with the linker comprising one thymidine residue being inserted between the cross-linking adapter sequence and the single-stranded nucleic acid, Example 4 which was the product with one cross-link (CL1) with the linker comprising eight thymidine residues being inserted, and Example 3 which was product with one cross-link (CL1) with the propyl linker being inserted exhibited a slightly lower Tm value then Example 1 which was also the product with one cross-link (CL1) but maintained a higher Tm value than the double stranded product with no cross-links. These results demonstrate the double stranded part stabilized by the cross-linking is able to produce the stabilization effect even in the case in which the double stranded part is not directly bound to the hybridization region.

As shown in FIG. 9, Comparative Example 8 which had the double-stranded adapter sequence exhibited Tm comparable to Comparative Example 7 which had the single-stranded adapter sequence. Further, Comparative Example 9 which had the hairpin loop also exhibited Tm comparable to Comparative Example 7 which had the single-stranded adapter sequence. On the other hand, Examples 11 and 12 which had the cross-linking adapter sequence exhibited a higher Tm value by 10° C. or more as compared with Comparative Examples 6 to 9. Further, the chimeric molecule of Example 12 (dr5'CL(12/34)) in which the single-stranded nucleic acid part is RNA and the cross-linking adapter sequence part is DNA exhibited a high Tm value.

As shown in FIG. 10, Comparative Examples 13, 15, and 17 which had the double-stranded adapter sequence exhibited a Tm value comparable to Comparative Examples 11 and 16 which had the single-stranded adapter sequence. Further, Comparative Example 14 which had the hairpin loop also exhibited Tm comparable to Comparative Examples 11 and 16 which had the single-stranded adapter sequence. On the other hand, Examples 13 to 15 and 17 which had the cross-linking adapter sequence exhibited a higher Tm value by 10° C. or more as compared with Comparative Examples 10, 11, and 13 to 17; and Example 17 which was the product with two cross-links (CL2) exhibited a much higher Tm value.

It is to be noted in FIGS. 8 to 10 that, for the target RNA which make mismatched base pairs (miR21-M: SEQ ID NO: 2), the Tm value was all decreased but the effect of stabilizing hybridization appeared in the same way as for the target RNA with perfectly-matched base pairs (miR21: SEQ ID NO: 1).

From the above, it has been demonstrated that the product with one cross-link (CL1) and the product with two cross-links (CL2) according to the Examples stabilize the hybridization with the target nucleic acid. In addition, it has been confirmed that this effect of stabilizing hybridization is able to be attained regardless of whether the cross-linking adapter sequence is DNA, RNA, or 2'-OMe RNA.

Example C (Evaluation of miRNA-Suppression Activity)

2'-OMe RNA has excellent stability in cells and is used as an antisense. In view of this, Examples 14, 15, and 17 which were 2'-OMe RNA was evaluated for an inhibitory effect on a miRNA activity in cells. It is to be noted that miR-21 (SEQ ID NO: 1) was selected as a miRNA to be targeted.

A dual-luciferase assay system was employed to look at the inhibitory effect on miR-21. A vector was constructed as described below, which vector has a binding sequence for miR-21 introduced only to the 3' UTR of a sequence encoding Renilla luciferase in psiCHECK-2 (registered trademark) vector (Promega). First, a double-stranded oligonucleotide was synthesized, the double-stranded oligonucleotide corresponding to miR-21 with part of the cleavage recognition sequence of restriction enzyme sites SgfI and PmeI at both ends and a complementary strand thereof (SEQ ID NO: 47 and SEQ ID NO: 48). A phosphate group necessary for ligation to the vector was introduced to the 5' end of each oligonucleotide at the stage of the synthesis. Subsequently, to psiCHECK-2 (registered trademark) vector (Promega) that had been treated with SgfI (Promega) and PmeI (Promega), the above double stranded oligonucleotide that had been in advance annealed was ligated using T4 DNA ligase (Promega). The obtained vector is subjected to cloning and sequence confirmation by a common technique using *Escherichia coli*; and a vector with the binding sequence of miR-21 being inserted in an intended site (psiCHECK-2-miR-21) was obtained.

```
SEQ ID NO: 47:
5' pCGCAGTAGAGCTCTAGTTCAACATCAGTCTGATAAGCTAGTTT 3'
(p: phosphate)

SEQ ID NO: 48:
3' TAGCGTCATCTCGAGATCAAGTTGTAGTCAGACTATTCGATCAA
                                              Ap 5'
(p: phosphate)
```

When the psiCHECK-2-miR-21 vector is introduced to cells, miR-21 within cells binds to the 3' UTR of Renilla luciferase mRNA to inhibit the expression of *Renilla* luciferase; and no luminescence derived from the enzyme is detected. However, when a nucleic acid molecule (anti-miRNA oligonucleotide: AMO) that has a sequence complementary to miR-21 is introduced, the binding of miR-21 to mRNA is competitively inhibited and the expression of Renilla luciferase is induced to allow luminescence to be observed. HeLa cells express a large amount of miR-21. The cells were thus seeded at a concentration of 24 cells/well in a 96-well plate (Nunc) and cultured for 24 hours; and psiCHECK-2-miR-21 (0.1 mg/well) and the synthesized anti-miRNA oligonucleotide (0.05 to 50 nM/well) were introduced to the cells together with lipofectamine (registered trademark) 2000 (Life technologies, 0.3 mL/well). In addition, an experiment in which a vector (psiCHECK-2) having no miR-21 binding sequences was introduced to the cells was concurrently carried out as a positive control.

After the 24-hour culturing, the luminescence strength of each of Renilla and Firefly luciferases was measured by using a Dual-Glo (registered trademark) Luciferase assay system (Promega). A ratio (Rluc/Fluc) of the luminescence strength of Renilla luciferase with the luminescence strength of Firefly luciferase, which served as an internal control, was calculated and further normalized with a value calculated based on the vector having no miR-21 binding sequences. A relative value of Rluc/Fluc was plotted against the corresponding concentration of the anti-miRNA oligonucleotide to evaluate the inhibitory effect on the miRNA activity (FIG. 11). In addition, commercially-available anti-miRNA oligonucleotides (LNA-miRCURY, LNA NC, meridian, and Tough Decoy) were worked on the cells under the same conditions to examine the inhibitory effect on miRNA.

Commercially available anti-miRNA oligonucleotides used for comparison were shown below.

LNA-miRCURY (miRCURY, LNA miRNA inhibitor hsa-miR21, Exiqon)

LNA NC (miRCURY LNA microRNA Inhibitor Negative Control A, Exiqon)

meridian (miRIDIAN microRNA hsa-miR-21-5p hairpin inhibitor, GE Healthecare)

Tough decoy (MISSION, Synthetic microRNA Inhibitor Human hsa-miR-21-5p, Sigma)

The results are shown in FIG. 11A to D. It is to be noted that, as for the concentration of each molecule added in FIG. 11A to D, the four bars, from left to right, correspond 0 nM, 0.5 nM, 2 nM, and 10 nM.

As shown in FIG. 11A, Comparative Example 13 (m5'DS (12/34)) which had the double-stranded adapter sequence exhibited a higher miRNA-suppression activity, as compared with Comparative Example 10 (m-asmiR21) which did not have the double-stranded adapter sequence. In addition, Example 14 (m5'CL(12/34)) which had the cross-linking adapter sequence exhibited a much higher miRNA-suppression activity, as compared with Comparative Example 13 (m5'DS(12/34)) which had the double-stranded adapter sequence.

As shown in FIG. 11B, Comparative Example 15 (m3'DS (12/34) which had the double-stranded adapter sequence exhibited a higher miRNA-suppression activity, as compared with Comparative Example 10 (m-asmiR21) and 3'Me34U (the nucleic acid strand of SEQ ID NO: 44) which did not have the double-stranded adapter sequence. In addition, Example 15 (m3'CL(12/34)) which had the cross-linking adapter sequence exhibited a much higher miRNA-suppression activity, as compared with Comparative Example 15 (m3'DS(12/34) which had the double-stranded adapter sequence.

As shown in FIG. 11C, Comparative Example 17 (mDS2 (12×2/46)) which had the double-stranded adapter sequence at both ends exhibited a higher miRNA-suppression activity, as compared with Comparative Example 10 (m-asmiR21) and Comparative Example 16 (mSS(46)) which did not have the double-stranded adapter sequence. In addition, Example 17 (mCL2(12-I×2/46)) which had the cross-linking adapter sequence at both ends exhibited a much higher miRNA-suppression activity, as compared with Comparative Example 17 (mDS2(12×2/46)) which had the double-stranded adapter sequence. It is to be noted that Comparative Example 18 (mCL2(12-I×2/34)) in which a region hybridizing with miR-21 comprised about 10 bases exhibited a significantly decreased miRNA-suppression activity, implying thus stable binding with miRNA is important in order to attain a sufficient amount of miRNA-suppression activity.

As shown in FIG. 11D, Example 17 (mCL2(12-I×2/46)) which had the cross-linking adapter sequence at both ends exhibited a higher miRNA-suppression activity, as compared with LNA (miRCURY), LNA NC, miRIDIAN, and Tough Decoy. Even though the commercially available anti-miRNA oligonucleotides (LNA-miRCURY, LNA NC, meridian, Tough Decoy) also exhibited the suppression effect, mCL2(12-I×2/46) (Example 17) had a higher inhibitory effect than those and was confirmed to also function effectively in cells.

From the above, it has been demonstrated that the product with one cross-link (CL1) and the product with two cross-links (CL2) according to the Examples have a higher miRNA-suppression activity.

Example D

A complementary strand nucleic acid complex was prepared and a melting curve was measured. As a nucleic acid to be targeted, miR21 (SEQ ID NO: 1) was selected.

As Example 19, a complementary strand nucleic acid complex d5'CL(12/34)/dc34dU was prepared by mixing, at equimolar amounts, d5'CL(12/34) (Example 1) and the nucleic acid strand of SEQ ID NO: 49 which had a sequence complementary to the single-stranded region of d5'CL(12/34) to allow hybridization (FIG. 12A). A schematic diagram for d5'CL(12/34)/dc34dU (Example 19) is shown in FIG. 12B.

SEQ ID NO: 49: 5' TAGCTTATCAGACTGATGTT-GAGCTGCuGCTCCG 3'

As Example 20, a complementary strand nucleic acid complex d5'CL(12/34)/dcCL(12/34) was prepared by mixing, at equimolar amounts, d5'CL(12/34) (Example 1) and dcCL(12/34) which had a sequence complementary to a single-stranded region of d5'CL(12/34) and had the cross-linking adapter sequence to allow hybridization (FIG. 12A). dcCL(12/34) was prepared using a nucleic acid strand of SEQ ID NO: 50 and a nucleic acid strand of SEQ ID NO: 51 in the same manner as described for d5'CL(12/34) (Example 1). A schematic diagram for d'CL(12/34)/dcCL (12/34) (Example 20) is shown in FIG. 12C.

SEQ ID NO: 50: 5' TAGCTTATCAGACTGATGTTGAGCTGCXGC TCCG 3'
(X = u: deoxyuridine)

SEQ ID NO: 51: 3' CGACGXCGAGGC 5'
(X = u: deoxyuridine)

As Comparative Example 19, a molecule d34dU/dc34dU was prepared by mixing, at equimolar amounts, dc34dU (the nucleic acid strand of SEQ ID NO: 49) and a nucleic acid strand d34dU (SEQ ID NO: 52) which had a sequence complementary to dc34dU to allow hybridization (FIG. 12A).

SEQ ID NO: 52:
3' GCCTCGXCGTCGATCGAATAGTCTGACTACAACT 5'
(X = u: deoxyuridine)

With regard to Examples 19 and 20 and Comparative Example 19, Tm was measured by the same method as described in Example B. The results are shown in FIG. 12D. The complementary strand nucleic acid complex d5'CL(12/34)/dc34dU (Example 19) which had the cross-linking adapter exhibited a significantly higher Tm value (an increase by about 7° C.), as compared with the nucleic acid d34dU/dc34dU (Comparative Example 19) which had the single-stranded structure alone. Further, the complementary strand nucleic acid complex d5'CL(12/34)/dcCL(12/34) (Example 20) in which the nucleic acid molecules having the cross-linking adapter were together hybridized exhibited an additional increases in Tm to the same extent (an increase by about 7° C.), which confirmed a synergistic effect on Tm stabilization.

From the above, it has been demonstrated that the complementary strand nucleic acid complex according to this Example is stably hybridized.

Example E

With regard to Examples 14, 15, and 17 and Examples 21 to 23 (described later), each of which was 2'-OMe RNA, an inhibitory effect on a miRNA activity was evaluated 48 hours after transfection.

By the same method as described in Example A, the following molecules of Examples 21 to 23 were synthesized.

Figure 13:
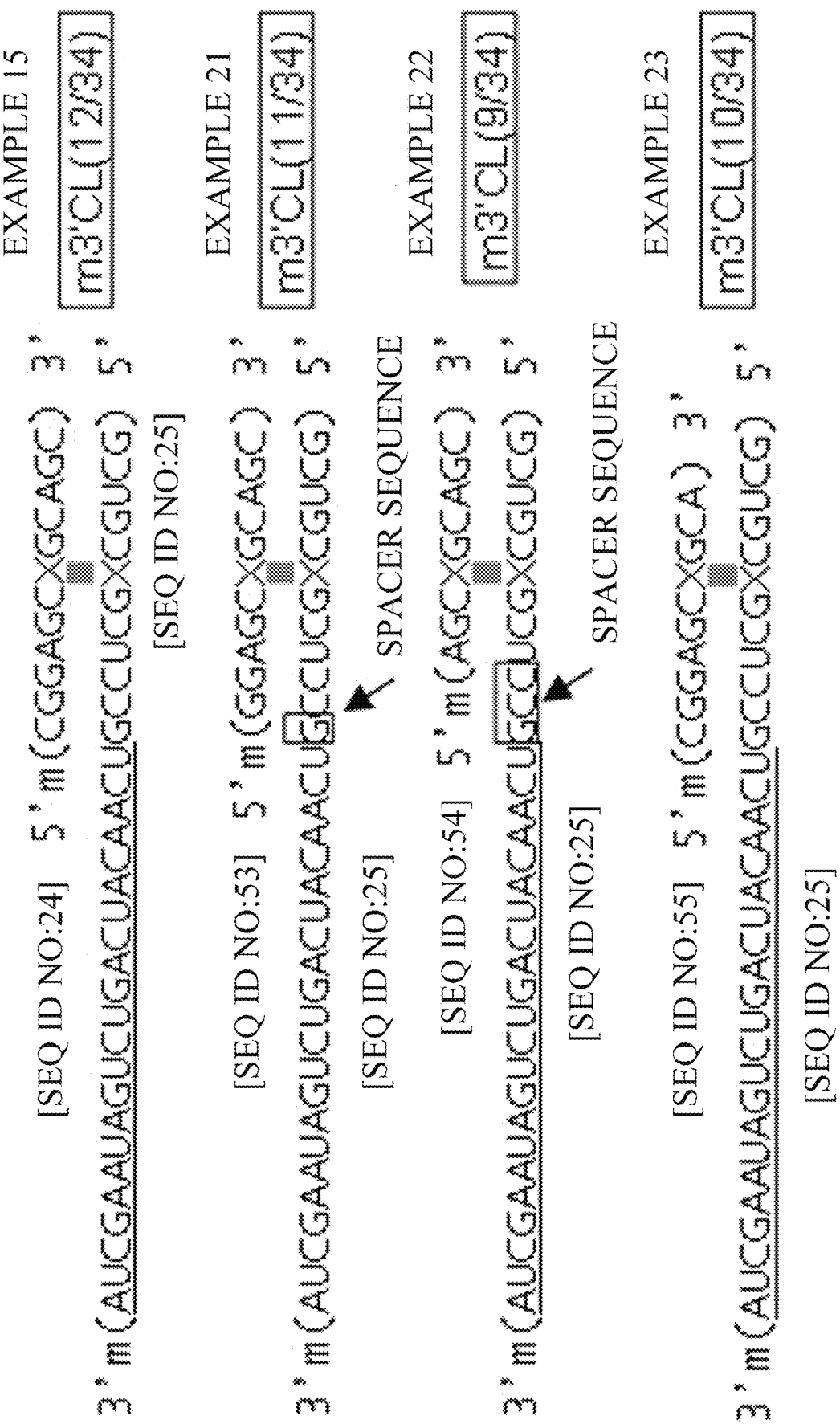
FIG. 13 is a figure showing the base sequence of the nucleic acid complexes (2'-OMe RNAs) of Examples 15 and 21 to 23.

As Example 21, m3'CL(11/34) which had a sequence complementary to miR21 (a complementary binding-like sequence) and a 11-mer double-stranded cross-linking adapter sequence with, as a spacer (linker), a G (guanine) residue therebetween was synthesized (FIG. 13).

As Example 22, m3'CL(9/34) which had a sequence complementary to miR21 (a complementary binding-like sequence) and a 9-mer double-stranded cross-linking adapter sequence with, as a spacer (linker), a 3-mer oligonucleotide (GCC) therebetween was synthesized (FIG. 13).

As Example 23, m3'CL(10/34) which had a sequence complementary to miR21 (a complementary binding-like sequence) and a 10-mer double-stranded cross-linking adapter sequence was synthesized (FIG. 13).

In order to prepare the molecules of Examples 21 to 23, each of oligonucleotides shown in Table 6 was used. With regard to "m" and "X", the same as described in Example A is also applied here.

TABLE 6

| Example 21 m3' CL(11/34) | 5' m(GGAGCXGCAGC) 3' | SEQ ID NO: 53 |
|---|---|---|
| | 3' m(AUCGAAUAGUCUGACUACAACUGCCUCGXCGUCG) 5' | SEQ ID NO: 25 |
| Example 22 m3' CL(9/34) | 5' m(AGCXGCAGC) 3' | SEQ ID NO: 54 |
| | 3' m(AUCGAAUAGUCUGACUACAACUGCCUCGXCGUCG) 5' | SEQ ID NO: 25 |
| Example 23 m3' CL (10/34) | 5' m(CGGAGCXGCA) 3' | SEQ ID NO: 55 |
| | 3' m(AUCGAAUAGUCUGACUACAACUGCCUCGXCGUCG) 5' | SEQ ID NO: 25 |

To look at an inhibitory effect on miR-21, the dual-luciferase assay system as described in Example C was employed and carried out in the same manner as described in Example C. Transfection was also carried out in the same manner as described in Example C.

Forty-eight hours after the culturing, the inhibitory effect on an miR-21 activity was evaluated by the same method as described in Example C (FIG. 14).

As for miRIDIAN and Tough decoy which were used for a comparison purpose, the evaluation was carried out in the same manner as described in Example C.

Figure 14A:
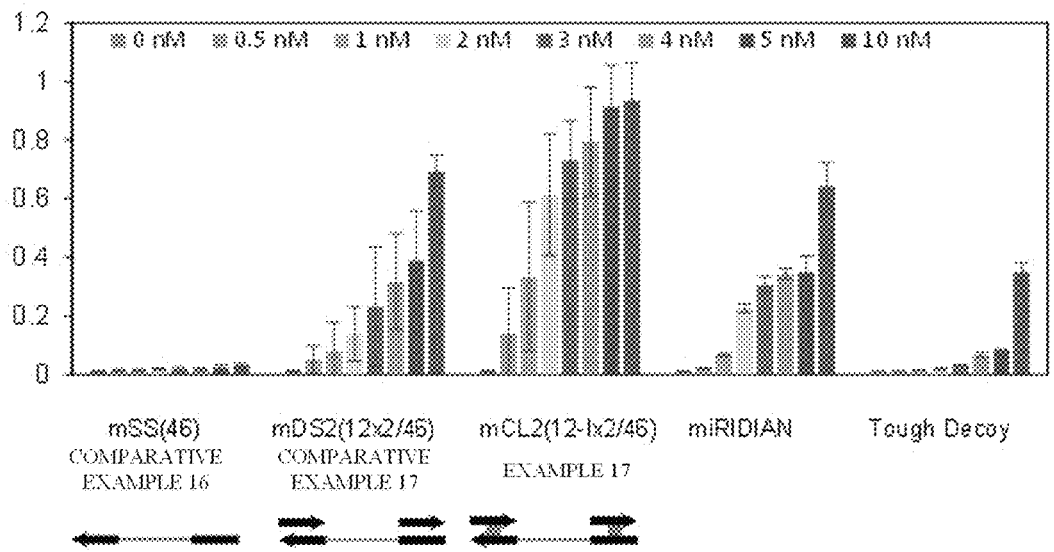
FIG. 14A is a figure showing the result of measurement of miRNA-suppression activity 48 hours after transfection for the nucleic acid complex of Example 17.

The results are shown in FIGS. 14A and B. It is to be noted that, as for the concentration of each molecule added in FIGS. 14A and B, the bars, from left to right, correspond 0 nM, 0.5 nM, 1 nM, 2 nM, 3 nM, 4 nM, 5 nM, and 10 nM.

As shown in FIG. 14A, as compared with Comparative Example 17 (mDS2(12×2/46)) which had the simple double-stranded adapter sequence, Example 17 (mCL2(12-I×2/46)) which had the cross-linking adapter sequence exhibits a higher miRNA-suppression activity; and a difference in the miRNA-suppression activity became more apparent, as compared with the counterpart 24 hour after transfection. This suggests that the product with cross-links (Example 17) has a more sustained miRNA-suppression activity.

Figure 14B:
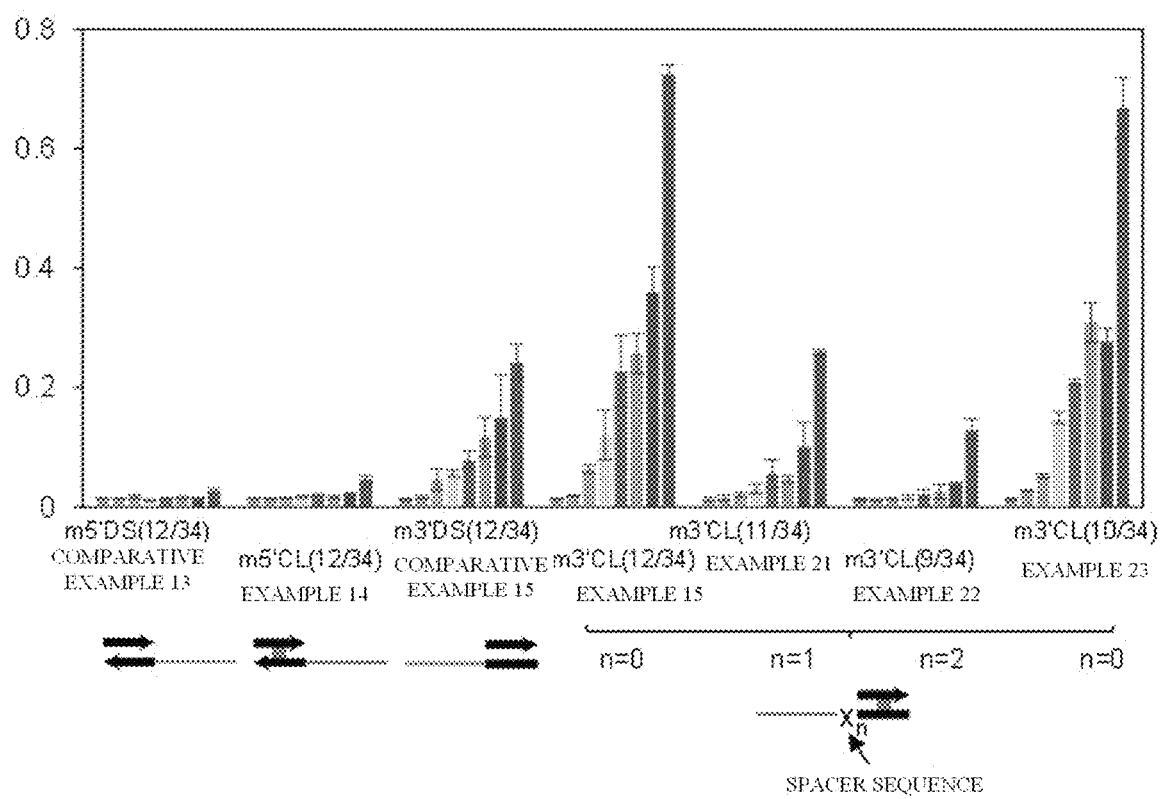
FIG. 14B is a figure showing the results of measurement of miRNA-suppression activity 48 hours after transfection for the nucleic acid complexes of Examples 14, 15, and 21 to 23.

As shown in FIG. 14B, when compared with Example 14 (m5'CL(12/34)) which had the cross-linking adapter sequence at the 3' end of the complementary binding-like sequence (single-stranded nucleic acid), Example 21 (m3'CL(11/34)), Example 22 (m3'CL(9/34)), and Example 23 (m3'CL(10/34)) which had the cross-linking adapter sequence at the 5' terminal side of the complementary binding-like sequence (single-stranded nucleic acid) exhibited a higher miRNA-suppression activity. Further, when the results at 48 hour after transfection were compared with those at 24 hour after transfection, a difference in the miRNA-suppression activity was found more significant, revealing that the structure with the cross-linking adapter sequence at the 5' terminal side of the complementary binding-like sequence (single-stranded nucleic acid) is important. Further, when compared with Example 21 (m3'CL(11/34)) and Example 22 (m3'CL(9/34)) which had the spacer (linker) between the sequence complementary to miR21 (a complementary binding-like sequence) (single-stranded nucleic acid) and the cross-linking adapter sequence, Example 23 (m3'CL(10/34)) which did not have such a spacer exhibited a higher miRNA-suppression activity, revealing that the miRNA-suppression activity was higher in the case in which the complementary binding-like sequence (single-stranded nucleic acid) came directly next to the cross-linking adapter sequence without the spacer.

From the above, it has been demonstrated that the product with one cross-link (CL1) which had the cross-linking adapter sequence at the 5' terminal side of the complementary binding-like sequence (single-stranded nucleic acid) had a higher miRNA-suppression activity.

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

The present application is based on Japanese Patent Application No. 2014-251847 filed on Dec. 12, 2014 and includes the specifications, claims, drawings, and abstract thereof. The disclosure in the above Japanese Patent Application is incorporated in the present specification by reference in their entirety.

INDUSTRIAL APPLICABILITY

The stabilization effect on the hybridization by the cross-linked double stranded structure of the present disclosure is believed to be useful in improving sensitivity of nucleic acid detection with RNA, DNA, or the like as a target and producing high pharmacological effects in nucleic acid medicines. In addition, because the present disclosure is a unique nucleic acid structure, it is possible to use in combination with various existing nucleic acid derivative monomers and to further improve effects of existing techniques. This enables the new structure of the nucleic acid of the present disclosure to use across a wide range of areas utilizing nucleic acids and to also offer high availability in industries.

SEQUENCE LISTING

15F074-PCT_Sequence Listing.txt

The invention claimed is:

1. A method of stabilizing hybridization between a target nucleic acid and a nucleic acid complex, comprising:
    hybridizing the nucleic acid complex with the target nucleic acid,
    wherein the target nucleic acid has a total length of 5 to 30 nucleotides,
    wherein the nucleic acid complex comprises:
    a single-stranded nucleic acid comprising a base sequence that is capable of being paired with a base sequence of the target nucleic acid, wherein the base sequence of the single-stranded nucleic acid is capable of being paired with 70% to 100% of the total length of the target nucleic acid sequence; and
    a cross-linked double-stranded nucleic acid comprising a first nucleic acid strand linked to at least one of a 5' end and a 3' end of the single-stranded nucleic acid and a second nucleic acid strand comprising a base sequence that is paired with 70% to 100% of a base sequence of the first nucleic acid strand,
    wherein the hybridizing the nucleic acid complex with the target nucleic acid comprises hybridizing the single-stranded nucleic acid with the target nucleic acid,
    wherein the cross-linked double-stranded nucleic acid is cross-linked by a bond between sugars of the first nucleic acid strand and the second nucleic acid strand,
    wherein the sugars of the first nucleic acid strand and the second nucleic acid strand are linked by a cross-linking reagent having an aminooxy group or an amino group,
    wherein the cross-linking reagent is a compound represented by a general formula 1: $R_1$—NH—O-$L_1$-D-$L_2$-A (1)
    wherein
    $R_1$ is a hydrogen atom, an alkyl group, or a protective group of an amino group,
    D is an aromatic group selected from the group consisting of a substituted or unsubstituted phenylene group, a substituted or unsubstituted anthrylene group, a substituted or unsubstituted naphthylene group, a substituted or unsubstituted phenanthrylene group, a substituted or unsubstituted anthraquinolylene group, and a substituted or unsubstituted acridinylene group, or a $C_{2-10}$ alkyl group,
    a substituent of the aromatic group is selected from the group consisting of a halogen atom, a $C_{1-6}$ alkyl group, a nitro group, a cyano group, a $C_{2-6}$ alkenyl group, a $C_{3-10}$ cycloalkyl group, a $C_{1-10}$ alkoxy group, and a $C_{1-10}$ acyl group,
    $L_1$ is a direct bond or a divalent group represented by the following general formula 3 or 4;

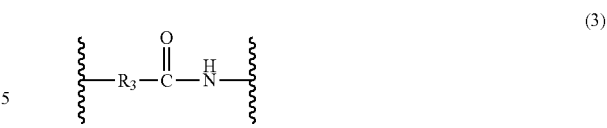

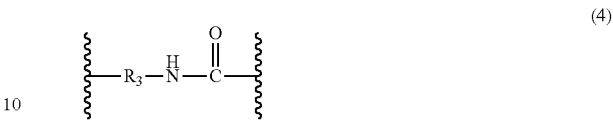

wherein $R_3$ is a $C_{2-9}$ alkylene group or —$(CH_2)_o$—$(OCH_2CH_2)_p$-$(CH_2)_q$—, o to q are each independently an integer of 0 to 15, o+p+q is 1 to 15,
$L_2$ is a direct bond or a divalent group represented by the following general formula 5 or 6:

wherein $R_4$ is a $C_{2-9}$ alkylene group or —$(CH_2)_r$—$(OCH_2CH_2)_s$—$(CH_2)_t$—, r to t are each independently an integer of 0 to 15, r+s+t is 1 to 15, and
A is an aminooxy group or a protected aminooxy group; or a salt thereof.

2. The method according to claim 1, wherein the cross-linked double-stranded nucleic acid is linked to the 5' end of the single-stranded nucleic acid.

3. The method according to claim 1, wherein the cross-linking reagent comprises an aminooxy group, and wherein aldehyde groups in the sugars of the first nucleic acid strand and the second nucleic acid strand are linked via the aminooxy group of the cross-linking reagent in the cross-linked double-stranded nucleic acid.

4. The method according to claim 1,
    wherein the nucleic acid complexes stably hybridizes with the target nucleic acid in a buffer that includes 10 mM NaCl and 10 mM Na cacodylate and has a pH of 7.0.

* * * * *

```
                        SEQUENCE LISTING

<160> NUMBER OF SEQ ID NOS: 55

<210> SEQ ID NO 1
<211> LENGTH: 22
<212> TYPE: RNA
<213> ORGANISM: Artificial Sequence
<220> FEATURE:
<223> OTHER INFORMATION: miR21

<400> SEQUENCE: 1
uagcuuauca gacugauguu ga                                                  22

<210> SEQ ID NO 2
<211> LENGTH: 22
<212> TYPE: RNA
<213> ORGANISM: Artificial Sequence
<220> FEATURE:
<223> OTHER INFORMATION: miR21-M

<400> SEQUENCE: 2
uagcuuauca cacugauguu ga                                                  22

<210> SEQ ID NO 3
<211> LENGTH: 12
<212> TYPE: DNA
<213> ORGANISM: Artificial Sequence
<220> FEATURE:
<223> OTHER INFORMATION: synthetic DNA
<220> FEATURE:
<221> NAME/KEY: misc_feature
<222> LOCATION: (7)..(7)
<223> OTHER INFORMATION: n is deoxyuridine

<400> SEQUENCE: 3
cggagcngca gc                                                             12

<210> SEQ ID NO 4
<211> LENGTH: 34
<212> TYPE: DNA
<213> ORGANISM: Artificial Sequence
<220> FEATURE:
<223> OTHER INFORMATION: synthetic DNA
<220> FEATURE:
<221> NAME/KEY: misc_feature
<222> LOCATION: (28)..(28)
<223> OTHER INFORMATION: n is deoxyuridine

<400> SEQUENCE: 4
tcaacatcag tctgataagc tagctgcngc tccg                                     34

<210> SEQ ID NO 5
<211> LENGTH: 35
<212> TYPE: DNA
<213> ORGANISM: Artificial Sequence
<220> FEATURE:
<223> OTHER INFORMATION: synthetic DNA
<220> FEATURE:
<221> NAME/KEY: misc_feature
<222> LOCATION: (29)..(29)
<223> OTHER INFORMATION: n is deoxyuridine

<400> SEQUENCE: 5
tcaacatcag tctgataagc tatgctgcng ctccg                                    35
```

<210> SEQ ID NO 6
<211> LENGTH: 12
<212> TYPE: DNA
<213> ORGANISM: Artificial Sequence
<220> FEATURE:
<223> OTHER INFORMATION: synthetic DNA
<220> FEATURE:
<221> NAME/KEY: misc_feature
<222> LOCATION: (6)..(6)
<223> OTHER INFORMATION: n is deoxyuridine

<400> SEQUENCE: 6
gctgcngctc cg                                                            12

<210> SEQ ID NO 7
<211> LENGTH: 22
<212> TYPE: DNA
<213> ORGANISM: Artificial Sequence
<220> FEATURE:
<223> OTHER INFORMATION: synthetic DNA

<400> SEQUENCE: 7
tcaacatcag tctgataagc ta                                                 22

<210> SEQ ID NO 8
<211> LENGTH: 42
<212> TYPE: DNA
<213> ORGANISM: Artificial Sequence
<220> FEATURE:
<223> OTHER INFORMATION: synthetic DNA
<220> FEATURE:
<221> NAME/KEY: misc_feature
<222> LOCATION: (36)..(36)
<223> OTHER INFORMATION: n is deoxyuridine

<400> SEQUENCE: 8
tcaacatcag tctgataagc tattttttt gctgcngctc cg                            42

<210> SEQ ID NO 9
<211> LENGTH: 12
<212> TYPE: DNA
<213> ORGANISM: Artificial Sequence
<220> FEATURE:
<223> OTHER INFORMATION: synthetic DNA
<220> FEATURE:
<221> NAME/KEY: misc_feature
<222> LOCATION: (7)..(7)
<223> OTHER INFORMATION: n is deoxyuridine

<400> SEQUENCE: 9
cggtgcngca gc                                                            12

<210> SEQ ID NO 10
<211> LENGTH: 12
<212> TYPE: DNA
<213> ORGANISM: Artificial Sequence
<220> FEATURE:
<223> OTHER INFORMATION: synthetic DNA
<220> FEATURE:
<221> NAME/KEY: misc_feature
<222> LOCATION: (7)..(7)
<223> OTHER INFORMATION: n is deoxyuridine

<400> SEQUENCE: 10
cggagcngct gc                                                            12

<210> SEQ ID NO 11
<211> LENGTH: 12

```
<212> TYPE: DNA
<213> ORGANISM: Artificial Sequence
<220> FEATURE:
<223> OTHER INFORMATION: synthetic DNA
<220> FEATURE:
<221> NAME/KEY: misc_feature
<222> LOCATION: (1)..(1)
<223> OTHER INFORMATION: n is deoxyuridine

<400> SEQUENCE: 11
nggagccgca gc                                                              12

<210> SEQ ID NO 12
<211> LENGTH: 37
<212> TYPE: DNA
<213> ORGANISM: Artificial Sequence
<220> FEATURE:
<223> OTHER INFORMATION: synthetic DNA
<220> FEATURE:
<221> NAME/KEY: misc_feature
<222> LOCATION: (34)..(34)
<223> OTHER INFORMATION: n is deoxyuridine

<400> SEQUENCE: 12
tcaacatcag tctgataagc tagctgcggc tccnttt                                   37

<210> SEQ ID NO 13
<211> LENGTH: 50
<212> TYPE: DNA
<213> ORGANISM: Artificial Sequence
<220> FEATURE:
<223> OTHER INFORMATION: synthetic DNA
<220> FEATURE:
<221> NAME/KEY: misc_feature
<222> LOCATION: (28)..(28)
<223> OTHER INFORMATION: n is deoxyuridine
<220> FEATURE:
<221> NAME/KEY: misc_feature
<222> LOCATION: (45)..(45)
<223> OTHER INFORMATION: n is deoxyuridine

<400> SEQUENCE: 13
tcaacatcag tctgataagc tagctgcngc tccgttttcg gagcngcagc                     50

<210> SEQ ID NO 14
<211> LENGTH: 12
<212> TYPE: DNA
<213> ORGANISM: Artificial Sequence
<220> FEATURE:
<223> OTHER INFORMATION: synthetic DNA
<220> FEATURE:
<221> NAME/KEY: misc_feature
<222> LOCATION: (6)..(6)
<223> OTHER INFORMATION: n is deoxyuridine

<400> SEQUENCE: 14
gtgcgngatc ga                                                              12

<210> SEQ ID NO 15
<211> LENGTH: 46
<212> TYPE: DNA
<213> ORGANISM: Artificial Sequence
<220> FEATURE:
<223> OTHER INFORMATION: synthetic DNA
<220> FEATURE:
<221> NAME/KEY: misc_feature
<222> LOCATION: (7)..(7)
<223> OTHER INFORMATION: n is deoxyuridine
<220> FEATURE:
<221> NAME/KEY: misc_feature
<222> LOCATION: (40)..(40)
```

<223> OTHER INFORMATION: n is deoxyuridine

<400> SEQUENCE: 15
tcgatcncgc actcaacatc agtctgataa gctagctgcn gctccg        46

<210> SEQ ID NO 16
<211> LENGTH: 12
<212> TYPE: DNA
<213> ORGANISM: Artificial Sequence
<220> FEATURE:
<223> OTHER INFORMATION: synthetic DNA
<220> FEATURE:
<221> NAME/KEY: misc_feature
<222> LOCATION: (3)..(3)
<223> OTHER INFORMATION: n is deoxyuridine
<220> FEATURE:
<221> NAME/KEY: misc_feature
<222> LOCATION: (10)..(10)
<223> OTHER INFORMATION: n is deoxyuridine

<400> SEQUENCE: 16
cgnagcggcn gc        12

<210> SEQ ID NO 17
<211> LENGTH: 34
<212> TYPE: DNA
<213> ORGANISM: Artificial Sequence
<220> FEATURE:
<223> OTHER INFORMATION: synthetic DNA
<220> FEATURE:
<221> NAME/KEY: misc_feature
<222> LOCATION: (25)..(25)
<223> OTHER INFORMATION: n is deoxyuridine
<220> FEATURE:
<221> NAME/KEY: misc_feature
<222> LOCATION: (32)..(32)
<223> OTHER INFORMATION: n is deoxyuridine

<400> SEQUENCE: 17
tcaacatcag tctgataagc tagcngccgc tncg        34

<210> SEQ ID NO 18
<211> LENGTH: 12
<212> TYPE: RNA
<213> ORGANISM: Artificial Sequence
<220> FEATURE:
<223> OTHER INFORMATION: synthetic RNA
<220> FEATURE:
<221> NAME/KEY: misc_feature
<222> LOCATION: (7)..(7)
<223> OTHER INFORMATION: n is deoxyuridine

<400> SEQUENCE: 18
cggagcngca gc        12

<210> SEQ ID NO 19
<211> LENGTH: 34
<212> TYPE: RNA
<213> ORGANISM: Artificial Sequence
<220> FEATURE:
<223> OTHER INFORMATION: synthetic RNA
<220> FEATURE:
<221> NAME/KEY: misc_feature
<222> LOCATION: (28)..(28)
<223> OTHER INFORMATION: n is deoxyuridine

<400> SEQUENCE: 19
ucaacaucag ucugauaagc uagcugcngc uccg        34

```
<210> SEQ ID NO 20
<211> LENGTH: 12
<212> TYPE: RNA
<213> ORGANISM: Artificial Sequence
<220> FEATURE:
<223> OTHER INFORMATION: synthetic RNA
<220> FEATURE:
<221> NAME/KEY: misc_feature
<222> LOCATION: (7)..(7)
<223> OTHER INFORMATION: n is deoxyuridine

<400> SEQUENCE: 20
cggagcngca gc                                                          12

<210> SEQ ID NO 21
<211> LENGTH: 34
<212> TYPE: DNA
<213> ORGANISM: Artificial Sequence
<220> FEATURE:
<223> OTHER INFORMATION: synthetic DNA and RNA
<220> FEATURE:
<221> NAME/KEY: misc_feature
<222> LOCATION: (1)..(22)
<223> OTHER INFORMATION: RNA
<220> FEATURE:
<221> NAME/KEY: misc_feature
<222> LOCATION: (23)..(34)
<223> OTHER INFORMATION: DNA
<220> FEATURE:
<221> NAME/KEY: misc_feature
<222> LOCATION: (28)..(28)
<223> OTHER INFORMATION: n is deoxyuridine

<400> SEQUENCE: 21
ucaacaucag ucugauaagc uagctgcngc tccg                                  34

<210> SEQ ID NO 22
<211> LENGTH: 10
<212> TYPE: RNA
<213> ORGANISM: Artificial Sequence
<220> FEATURE:
<223> OTHER INFORMATION: synthetic RNA
<220> FEATURE:
<221> NAME/KEY: misc_feature
<222> LOCATION: (1)..(10)
<223> OTHER INFORMATION: 2'-0-methyl RNA
<220> FEATURE:
<221> NAME/KEY: misc_feature
<222> LOCATION: (7)..(7)
<223> OTHER INFORMATION: n is deoxyuridine

<400> SEQUENCE: 22 cggagcngca                                                             10

<210> SEQ ID NO 23
<211> LENGTH: 34
<212> TYPE: RNA
<213> ORGANISM: Artificial Sequence
<220> FEATURE:
<223> OTHER INFORMATION: synthetic RNA
<220> FEATURE:
<221> NAME/KEY: misc_feature
<222> LOCATION: (1)..(34)
<223> OTHER INFORMATION: 2'-0-methyl RNA
<220> FEATURE:
<221> NAME/KEY: misc_feature
<222> LOCATION: (28)..(28)
<223> OTHER INFORMATION: n is deoxyuridine

<400> SEQUENCE: 23
ucaacaucag ucugauaagc uagcugcngc uccg                                  34
```

```
<210> SEQ ID NO 24
<211> LENGTH: 12
<212> TYPE: RNA
<213> ORGANISM: Artificial Sequence
<220> FEATURE:
<223> OTHER INFORMATION: synthetic RNA
<220> FEATURE:
<221> NAME/KEY: misc_feature
<222> LOCATION: (1)..(12)
<223> OTHER INFORMATION: 2'-0-methyl RNA
<220> FEATURE:
<221> NAME/KEY: misc_feature
<222> LOCATION: (7)..(7)
<223> OTHER INFORMATION: n is deoxyuridine

<400> SEQUENCE: 24
cggagcngca gc                                                           12

<210> SEQ ID NO 25
<211> LENGTH: 34
<212> TYPE: RNA
<213> ORGANISM: Artificial Sequence
<220> FEATURE:
<223> OTHER INFORMATION: synthetic RNA
<220> FEATURE:
<221> NAME/KEY: misc_feature
<222> LOCATION: (1)..(34)
<223> OTHER INFORMATION: 2'-0-methyl RNA
<220> FEATURE:
<221> NAME/KEY: misc_feature
<222> LOCATION: (6)..(6)
<223> OTHER INFORMATION: n is deoxyuridine

<400> SEQUENCE: 25
gcugcngcuc cgucaacauc agucugauaa gcua                                   34

<210> SEQ ID NO 26
<211> LENGTH: 34
<212> TYPE: RNA
<213> ORGANISM: Artificial Sequence
<220> FEATURE:
<223> OTHER INFORMATION: synthetic RNA
<220> FEATURE:
<221> NAME/KEY: misc_feature
<222> LOCATION: (1)..(34)
<223> OTHER INFORMATION: 2'-0-methyl RNA
<220> FEATURE:
<221> NAME/KEY: misc_feature
<222> LOCATION: (6)..(6)
<223> OTHER INFORMATION: n is deoxyuridine

<400> SEQUENCE: 26
gcugcngcuc cgucaacauc agucugauca gaua                                   34

<210> SEQ ID NO 27
<211> LENGTH: 46
<212> TYPE: RNA
<213> ORGANISM: Artificial Sequence
<220> FEATURE:
<223> OTHER INFORMATION: synthetic RNA
<220> FEATURE:
<221> NAME/KEY: misc_feature
<222> LOCATION: (1)..(46)
<223> OTHER INFORMATION: 2'-0-methyl RNA
<220> FEATURE:
<221> NAME/KEY: misc_feature
<222> LOCATION: (6)..(6)
<223> OTHER INFORMATION: n is deoxyuridine
<220> FEATURE:
<221> NAME/KEY: misc_feature
<222> LOCATION: (40)..(40)
<223> OTHER INFORMATION: n is deoxyuridine
```

<400> SEQUENCE: 27
gcugcngcuc cgucaacauc agucugauaa gcuagcugcn gcuccg         46

<210> SEQ ID NO 28
<211> LENGTH: 46
<212> TYPE: RNA
<213> ORGANISM: Artificial Sequence
<220> FEATURE:
<223> OTHER INFORMATION: synthetic RNA
<220> FEATURE:
<221> NAME/KEY: misc_feature
<222> LOCATION: (1)..(46)
<223> OTHER INFORMATION: 2'-0-methyl RNA
<220> FEATURE:
<221> NAME/KEY: misc_feature
<222> LOCATION: (6)..(6)
<223> OTHER INFORMATION: n is deoxyuridine
<220> FEATURE:
<221> NAME/KEY: misc_feature
<222> LOCATION: (40)..(40)
<223> OTHER INFORMATION: n is deoxyuridine

<400> SEQUENCE: 28
gcugcngcuc cgucaacauc agucugauca gauagcugcn gcuccg         46

<210> SEQ ID NO 29
<211> LENGTH: 34
<212> TYPE: DNA
<213> ORGANISM: Artificial Sequence
<220> FEATURE:
<223> OTHER INFORMATION: synthetic DNA
<220> FEATURE:
<221> NAME/KEY: misc_feature
<222> LOCATION: (28)..(28)
<223> OTHER INFORMATION: n is deoxyuridine

<400> SEQUENCE: 29
tcaacatcag tctgataagc tagctgcngc tccg                      34

<210> SEQ ID NO 30
<211> LENGTH: 12
<212> TYPE: DNA
<213> ORGANISM: Artificial Sequence
<220> FEATURE:
<223> OTHER INFORMATION: synthetic DNA

<400> SEQUENCE: 30
cggagcagca gc                                              12

<210> SEQ ID NO 31
<211> LENGTH: 50
<212> TYPE: DNA
<213> ORGANISM: Artificial Sequence
<220> FEATURE:
<223> OTHER INFORMATION: synthetic DNA

<400> SEQUENCE: 31
tcaacatcag tctgataagc tagctgcagc tccgttttcg gagctgcagc     50

<210> SEQ ID NO 32
<211> LENGTH: 12
<212> TYPE: DNA
<213> ORGANISM: Artificial Sequence
<220> FEATURE:
<223> OTHER INFORMATION: synthetic DNA

<400> SEQUENCE: 32
cggagcagca gc                                                          12

<210> SEQ ID NO 33
<211> LENGTH: 35
<212> TYPE: DNA
<213> ORGANISM: Artificial Sequence
<220> FEATURE:
<223> OTHER INFORMATION: synthetic DNA and RNA
<220> FEATURE:
<221> NAME/KEY: misc_feature
<222> LOCATION: (1)..(34)
<223> OTHER INFORMATION: DNA
<220> FEATURE:
<221> NAME/KEY: misc_feature
<222> LOCATION: (35)..(35)
<223> OTHER INFORMATION: RNA
<220> FEATURE:
<221> NAME/KEY: misc_feature
<222> LOCATION: (28)..(28)
<223> OTHER INFORMATION: n is deoxyuridine

<400> SEQUENCE: 33
tcaacatcag tctgataagc tagctgcngc tccgu                                 35

<210> SEQ ID NO 34
<211> LENGTH: 46
<212> TYPE: DNA
<213> ORGANISM: Artificial Sequence
<220> FEATURE:
<223> OTHER INFORMATION: synthetic DNA
<220> FEATURE:
<221> NAME/KEY: misc_feature
<222> LOCATION: (7)..(7)
<223> OTHER INFORMATION: n is deoxyuridine
<220> FEATURE:
<221> NAME/KEY: misc_feature
<222> LOCATION: (40)..(40)
<223> OTHER INFORMATION: n is deoxyuridine

<400> SEQUENCE: 34
tcgatcncgc actcaacatc agtctgataa gctagctgcn gctccg                     46

<210> SEQ ID NO 35
<211> LENGTH: 22
<212> TYPE: RNA
<213> ORGANISM: Artificial Sequence
<220> FEATURE:
<223> OTHER INFORMATION: synthetic RNA

<400> SEQUENCE: 35
ucaacaucag ucugauaagc ua                                               22

<210> SEQ ID NO 36
<211> LENGTH: 34
<212> TYPE: RNA
<213> ORGANISM: Artificial Sequence
<220> FEATURE:
<223> OTHER INFORMATION: synthetic RNA

<400> SEQUENCE: 36
ucaacaucag ucugauaagc uagcugcagc uccg                                  34

<210> SEQ ID NO 37
<211> LENGTH: 12
<212> TYPE: RNA
<213> ORGANISM: Artificial Sequence
<220> FEATURE:
<223> OTHER INFORMATION: synthetic RNA

<400> SEQUENCE: 37
cggagcugca gc                                                            12

<210> SEQ ID NO 38
<211> LENGTH: 50
<212> TYPE: RNA
<213> ORGANISM: Artificial Sequence
<220> FEATURE:
<223> OTHER INFORMATION: synthetic RNA

<400> SEQUENCE: 38
ucaacaucag ucugauaagc uagcugcagc uccguuuucg gagcugcagc                   50

<210> SEQ ID NO 39
<211> LENGTH: 22
<212> TYPE: RNA
<213> ORGANISM: Artificial Sequence
<220> FEATURE:
<223> OTHER INFORMATION: synthetic RNA
<220> FEATURE:
<221> NAME/KEY: misc_feature
<222> LOCATION: (1)..(22)
<223> OTHER INFORMATION: 2'-O-methyl RNA

<400> SEQUENCE: 39
ucaacaucag ucugauaagc ua                                                 22

<210> SEQ ID NO 40
<211> LENGTH: 34
<212> TYPE: RNA
<213> ORGANISM: Artificial Sequence
<220> FEATURE:
<223> OTHER INFORMATION: synthetic RNA
<220> FEATURE:
<221> NAME/KEY: misc_feature
<222> LOCATION: (1)..(34)
<223> OTHER INFORMATION: 2'-O-methyl RNA
<220> FEATURE:
<221> NAME/KEY: misc_feature
<222> LOCATION: (28)..(28)
<223> OTHER INFORMATION: n is deoxyuridine

<400> SEQUENCE: 40
ucaacaucag ucugauaagc uagcugcngc uccg                                    34

<210> SEQ ID NO 41
<211> LENGTH: 34
<212> TYPE: RNA
<213> ORGANISM: Artificial Sequence
<220> FEATURE:
<223> OTHER INFORMATION: synthetic RNA
<220> FEATURE:
<221> NAME/KEY: misc_feature
<222> LOCATION: (1)..(34)
<223> OTHER INFORMATION: 2'-O-methyl RNA

<400> SEQUENCE: 41
ucaacaucag ucugauaagc uagcugcugc uccg                                    34

<210> SEQ ID NO 42
<211> LENGTH: 12
<212> TYPE: RNA
<213> ORGANISM: Artificial Sequence
<220> FEATURE:
<223> OTHER INFORMATION: synthetic RNA
<220> FEATURE:
<221> NAME/KEY: misc_feature
<222> LOCATION: (1)..(12)
<223> OTHER INFORMATION: 2'-O-methyl RNA

```
<400> SEQUENCE: 42
cggagcagca gc                                                      12

<210> SEQ ID NO 43
<211> LENGTH: 50
<212> TYPE: RNA
<213> ORGANISM: Artificial Sequence
<220> FEATURE:
<223> OTHER INFORMATION: synthetic RNA
<220> FEATURE:
<221> NAME/KEY: misc_feature
<222> LOCATION: (1)..(50)
<223> OTHER INFORMATION: 2'-O-methyl RNA

<400> SEQUENCE: 43
ucaacaucag ucugauaagc uagcugcugc uccguuuucg gagcagcagc              50

<210> SEQ ID NO 44
<211> LENGTH: 34
<212> TYPE: RNA
<213> ORGANISM: Artificial Sequence
<220> FEATURE:
<223> OTHER INFORMATION: synthetic RNA
<220> FEATURE:
<221> NAME/KEY: misc_feature
<222> LOCATION: (1)..(34)
<223> OTHER INFORMATION: 2'-O-methyl RNA

<400> SEQUENCE: 44
gcugcugcuc cgucaacauc agucugauaa gcua                              34

<210> SEQ ID NO 45
<211> LENGTH: 46
<212> TYPE: RNA
<213> ORGANISM: Artificial Sequence
<220> FEATURE:
<223> OTHER INFORMATION: synthetic RNA
<220> FEATURE:
<221> NAME/KEY: misc_feature
<222> LOCATION: (1)..(46)
<223> OTHER INFORMATION: 2'-O-methyl RNA

<400> SEQUENCE: 45
gcugcugcuc cgucaacauc agucugauaa gcuagcugcu gcuccg                 46

<210> SEQ ID NO 46
<211> LENGTH: 34
<212> TYPE: RNA
<213> ORGANISM: Artificial Sequence
<220> FEATURE:
<223> OTHER INFORMATION: synthetic RNA
<220> FEATURE:
<221> NAME/KEY: misc_feature
<222> LOCATION: (1)..(34)
<223> OTHER INFORMATION: 2'-O-methyl RNA
<220> FEATURE:
<221> NAME/KEY: misc_feature
<222> LOCATION: (6)..(6)
<223> OTHER INFORMATION: n is deoxyuridine
<220> FEATURE:
<221> NAME/KEY: misc_feature
<222> LOCATION: (28)..(28)
<223> OTHER INFORMATION: n is deoxyuridine

<400> SEQUENCE: 46
gcugcngcuc cgugauaagc uagcugcngc uccg                              34

<210> SEQ ID NO 47
<211> LENGTH: 43
```

<212> TYPE: DNA
<213> ORGANISM: Artificial Sequence
<220> FEATURE:
<223> OTHER INFORMATION: synthetic DNA

<400> SEQUENCE: 47
cgcagtagag ctctagttca acatcagtct gataagctag ttt                43

<210> SEQ ID NO 48
<211> LENGTH: 45
<212> TYPE: DNA
<213> ORGANISM: Artificial Sequence
<220> FEATURE:
<223> OTHER INFORMATION: synthetic DNA

<400> SEQUENCE: 48
aaactagctt atcagactga tgttgaacta gagctctact gcgat             45

<210> SEQ ID NO 49
<211> LENGTH: 34
<212> TYPE: DNA
<213> ORGANISM: Artificial Sequence
<220> FEATURE:
<223> OTHER INFORMATION: synthetic DNA
<220> FEATURE:
<221> NAME/KEY: misc_feature
<222> LOCATION: (28)..(28)
<223> OTHER INFORMATION: n is deoxyuridine

<400> SEQUENCE: 49
tagcttatca gactgatgtt gagctgcngc tccg                         34

<210> SEQ ID NO 50
<211> LENGTH: 34
<212> TYPE: DNA
<213> ORGANISM: Artificial Sequence
<220> FEATURE:
<223> OTHER INFORMATION: synthetic DNA
<220> FEATURE:
<221> NAME/KEY: misc_feature
<222> LOCATION: (28)..(28)
<223> OTHER INFORMATION: n is deoxyuridine

<400> SEQUENCE: 50
tagcttatca gactgatgtt gagctgcngc tccg                         34

<210> SEQ ID NO 51
<211> LENGTH: 12
<212> TYPE: DNA
<213> ORGANISM: Artificial Sequence
<220> FEATURE:
<223> OTHER INFORMATION: synthetic DNA
<220> FEATURE:
<221> NAME/KEY: misc_feature
<222> LOCATION: (7)..(7)
<223> OTHER INFORMATION: n is deoxyuridine

<400> SEQUENCE: 51
cggagcngca gc                                                 12

<210> SEQ ID NO 52
<211> LENGTH: 34
<212> TYPE: DNA
<213> ORGANISM: Artificial Sequence
<220> FEATURE:
<223> OTHER INFORMATION: synthetic DNA
<220> FEATURE:
<221> NAME/KEY: misc_feature
<222> LOCATION: (28)..(28)

<223> OTHER INFORMATION: n is deoxyuridine

<400> SEQUENCE: 52
tcaacatcag tctgataagc tagctgcngc tccg					34

<210> SEQ ID NO 53
<211> LENGTH: 11
<212> TYPE: RNA
<213> ORGANISM: Artificial Sequence
<220> FEATURE:
<223> OTHER INFORMATION: synthetic RNA
<220> FEATURE:
<221> NAME/KEY: misc_feature
<222> LOCATION: (1)..(11)
<223> OTHER INFORMATION: 2'-O-methyl RNA
<220> FEATURE:
<221> NAME/KEY: misc_feature
<222> LOCATION: (6)..(6)
<223> OTHER INFORMATION: n is deoxyuridine

<400> SEQUENCE: 53
ggagcngcag c					11

<210> SEQ ID NO 54
<211> LENGTH: 9
<212> TYPE: RNA
<213> ORGANISM: Artificial Sequence
<220> FEATURE:
<223> OTHER INFORMATION: synthetic RNA
<220> FEATURE:
<221> NAME/KEY: misc_feature
<222> LOCATION: (1)..(9)
<223> OTHER INFORMATION: 2'-O-methyl RNA
<220> FEATURE:
<221> NAME/KEY: misc_feature
<222> LOCATION: (4)..(4)
<223> OTHER INFORMATION: n is deoxyuridine

<400> SEQUENCE: 54 agcngcagc					9

<210> SEQ ID NO 55
<211> LENGTH: 10
<212> TYPE: RNA
<213> ORGANISM: Artificial Sequence
<220> FEATURE:
<223> OTHER INFORMATION: synthetic RNA
<220> FEATURE:
<221> NAME/KEY: misc_feature
<222> LOCATION: (1)..(10)
<223> OTHER INFORMATION: 2'-O-methyl RNA
<220> FEATURE:
<221> NAME/KEY: misc_feature
<222> LOCATION: (7)..(7)
<223> OTHER INFORMATION: n is deoxyuridine

<400> SEQUENCE: 55 cggagcngca					10